US011123292B2

(12) United States Patent
Beaudin

(10) Patent No.: US 11,123,292 B2
(45) Date of Patent: Sep. 21, 2021

(54) USE OF BIOCOMPATIBLE MICRODROPLETS FOR THE TREATMENT OF ATHEROSCLEROSIS, HEART DISEASE AND STROKE

(71) Applicant: Catherine Beaudin, Los Gatos, CA (US)

(72) Inventor: Catherine Beaudin, Los Gatos, CA (US)

(73) Assignee: Catherine S. Beaudin, Fremont, CA (US)

( * ) Notice: Subject to any disclaimer, the term of this patent is extended or adjusted under 35 U.S.C. 154(b) by 604 days.

(21) Appl. No.: 15/691,760

(22) Filed: Aug. 31, 2017

(65) Prior Publication Data

US 2018/0028443 A1 Feb. 1, 2018

Related U.S. Application Data

(63) Continuation-in-part of application No. 14/608,197, filed on Jan. 29, 2015, now abandoned.

(60) Provisional application No. 61/975,006, filed on Apr. 4, 2014, provisional application No. 61/932,781, filed on Jan. 29, 2014.

(51) Int. Cl.

| | |
|---|---|
| ***A61K 31/085*** | (2006.01) |
| ***A61K 31/09*** | (2006.01) |
| ***A61K 31/122*** | (2006.01) |
| ***A61K 31/235*** | (2006.01) |
| ***A61K 31/352*** | (2006.01) |
| ***A61K 47/02*** | (2006.01) |
| ***A61K 9/107*** | (2006.01) |
| ***A61K 9/00*** | (2006.01) |
| ***A61M 25/00*** | (2006.01) |
| ***A61M 1/36*** | (2006.01) |
| ***A61K 47/08*** | (2006.01) |
| ***A61K 47/14*** | (2017.01) |
| *A61M 1/34* | (2006.01) |

(52) U.S. Cl.

CPC .......... *A61K 9/1075* (2013.01); *A61K 9/0019* (2013.01); *A61K 31/085* (2013.01); *A61K 31/09* (2013.01); *A61K 31/122* (2013.01); *A61K 31/235* (2013.01); *A61K 31/352* (2013.01); *A61K 47/02* (2013.01); *A61K 47/08* (2013.01); *A61K 47/14* (2013.01); *A61M 1/369* (2013.01); *A61M 1/3687* (2013.01); *A61M 25/007* (2013.01); *A61M 1/342* (2013.01); *A61M 2202/0468* (2013.01); *A61M 2205/75* (2013.01)

(58) Field of Classification Search

CPC .. A61K 9/1075; A61K 9/0019; A61K 31/085; A61K 31/09; A61K 31/122; A61K 31/235; A61K 31/352; A61K 47/02; A61K 47/08; A61K 47/14; A61M 1/3687; A61M 1/369; A61M 25/007

USPC .......................................................... 514/65

See application file for complete search history.

(56) References Cited

U.S. PATENT DOCUMENTS

2002/0150615 A1* 10/2002 Sands .................... A61K 9/145 424/450

OTHER PUBLICATIONS

Baieth et al International Journal of biomedical science, 2008, 4(4), 323-329 (Year: 2008).*

Shipra Baluja et al., "Solubility of Cholesterol in some alcohols from 293.15 to 318.15K", Archives of Applied Science Research, 2009, 1 (2) pp. 263-270.

"Hansen's Solubility Parameters a Users Handbook" Second Edition, by Charles M. Hansen, CRC Press, pp. 1-9.

A. Huebner, S. Sharma, M. Srisa-Art, F. Hollfelder, J. Eden and A. deMello, "Microdroplets: A sea of applications", DOI: 10.1039/b806405a.

* cited by examiner

*Primary Examiner* — Yevgeny Valenrod

(57) ABSTRACT

A pharmacologically acceptable emulsion of biocompatible solvent microdroplets is provided for treating atherosclerosis, heart disease and stroke. Intravenous administration of the biocompatible solvent microdroplets enables the microdroplets to bind and dissolve free cholesterol, cholesterol esters or other fatty compounds within the plaque. A high level of selectivity is ensured from energy principals, by designing the microdroplets to have a low interfacial surface energy when binding to free cholesterol or cholesterol esters in arterial plaque and a high interfacial surface energy when coming into contact with blood cells or endothelial cells along the walls of blood vessels. A review of many compounds which may form the basis of the biocompatible solvent from which the microdroplets are fabricated, as well as their solubility parameters are provided. Furthermore, a specially designed catheter with a micromachined tip is also provided to allow the microdroplets to be generated directly within a blood vessel, as an alternative to emulsification.

20 Claims, 14 Drawing Sheets

FIG. 1: Operating Principal of Biocompatible Microdroplet Solvent
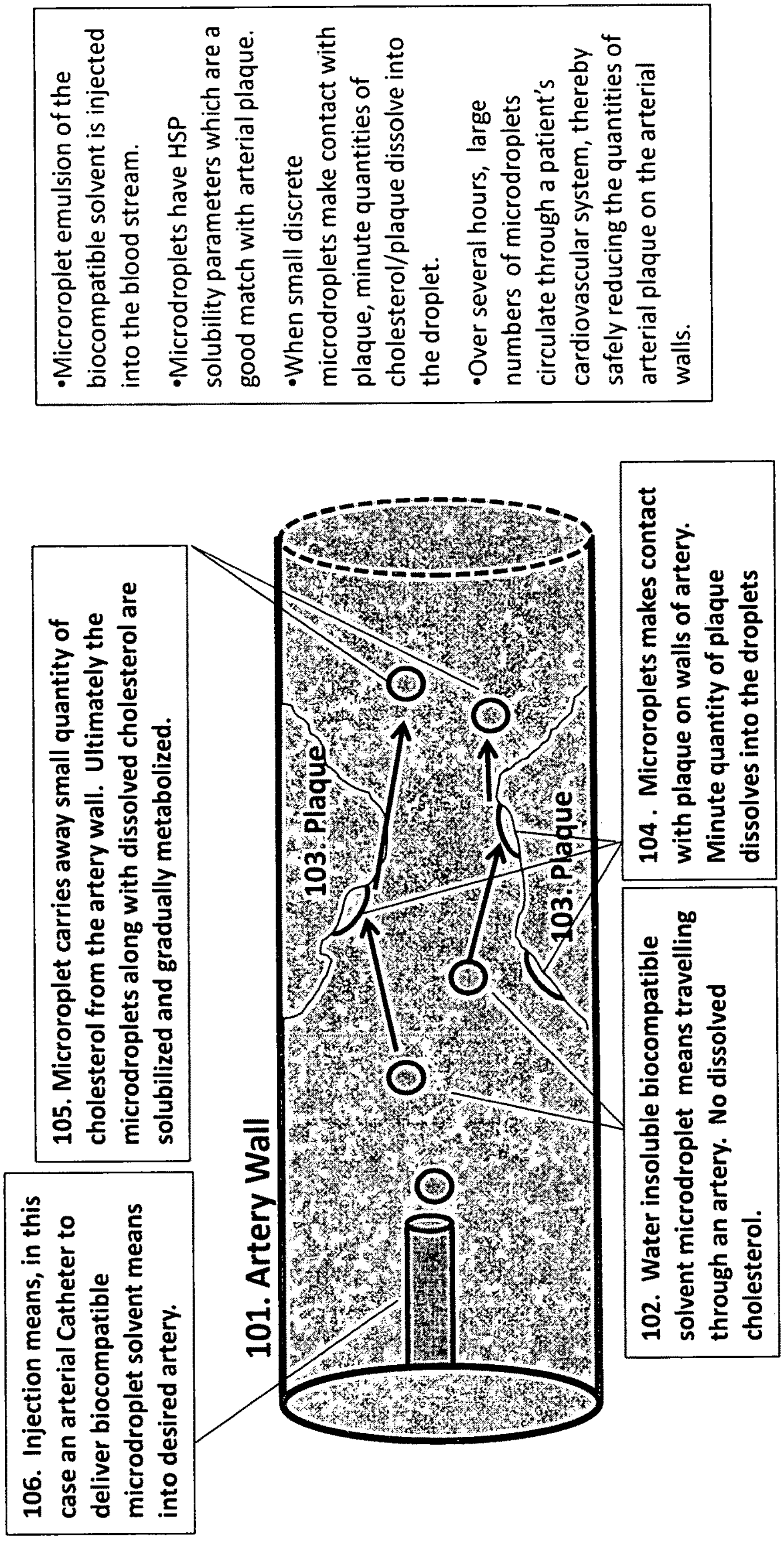

FIG. 2: Surface Energy of the Microdroplet / Cholesterol System

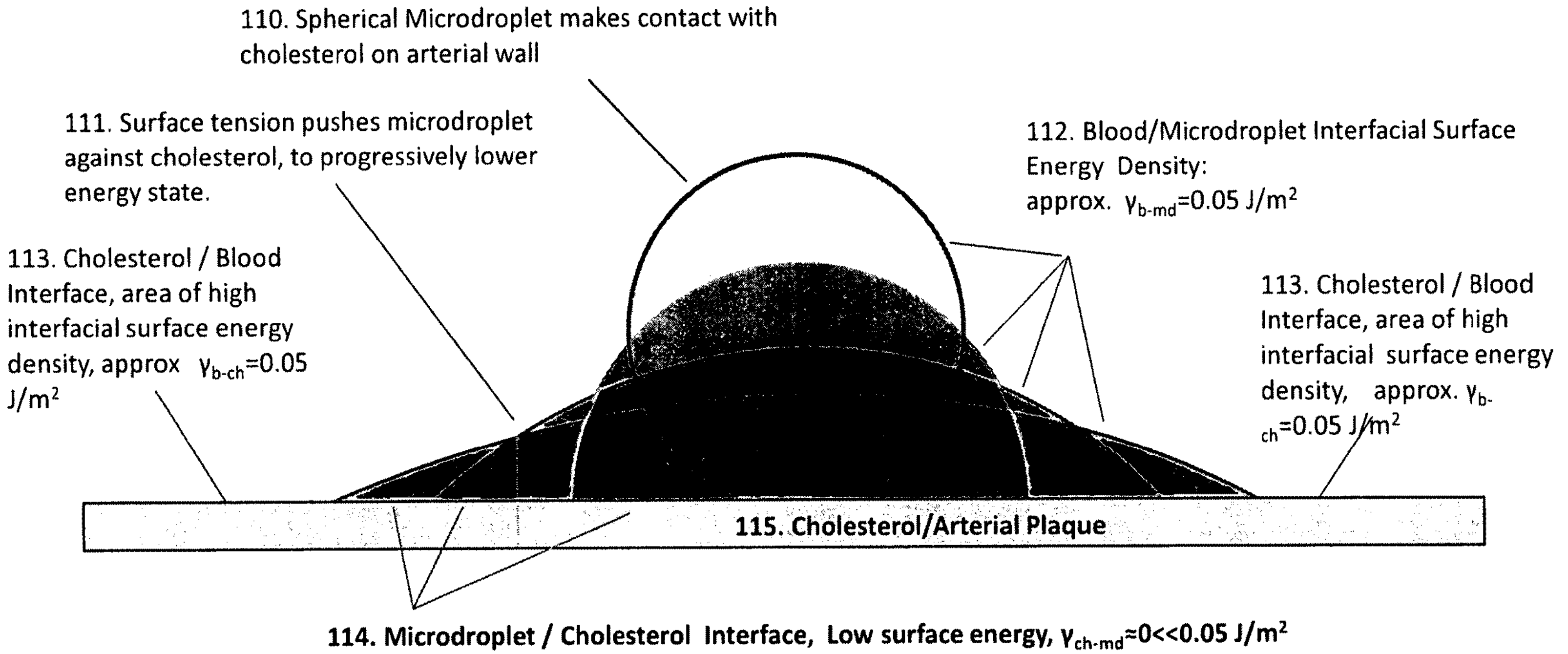

•Cholesterol and biocompatible microdroplets are assumed to have similar solubility properties, hence very minimal surface tension.

•As the droplet expands to cover the cholesterol, the total surface energy of the Microdroplet/Cholesterol system is reduced, surface tension holds the spreading microdroplet against the cholesterol, despite flowing blood.

- Energy principles can be used to derive the attractive forces, and internal pressure within the droplet as it deforms to cover the cholesterol on an arterial wall.

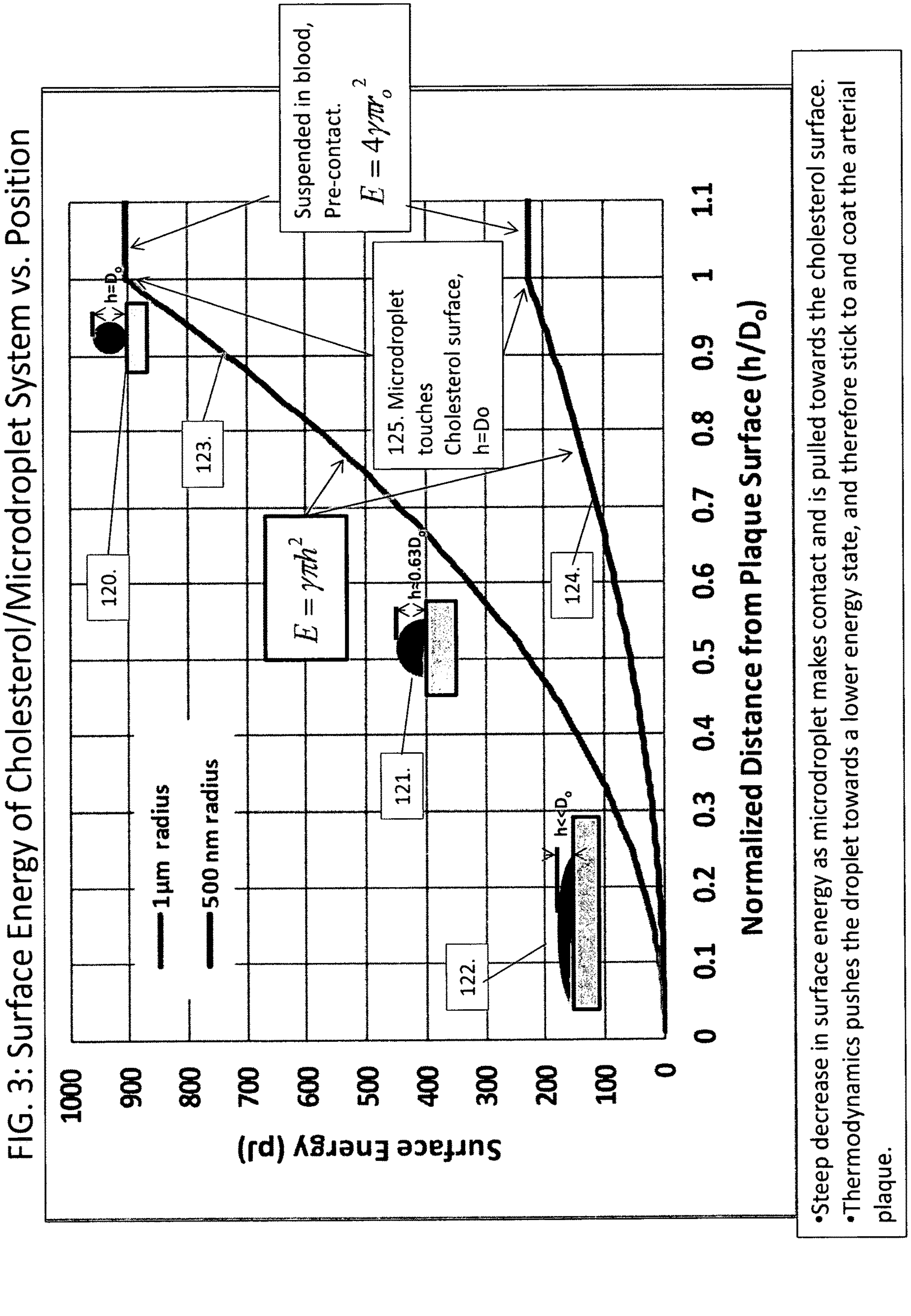
FIG. 3: Surface Energy of Cholesterol/Microdroplet System vs. Position
Surface Energy (pJ)
1000
900
800
700
600
500
400
300
200
100
0
0
0.1
0.2
0.3
0.4
0.5
0.6
0.7
0.8
0.9
1
1.1
Normalized Distance from Plaque Surface (h/D$_o$)
1μm radius
500 nm radius
Suspended in blood, Pre-contact.
$E = 4\gamma\pi r_o^2$
125. Microdroplet touches Cholesterol surface, h=Do
$E = \gamma\pi h^2$
h=D$_o$
h≈0.63D$_o$
h<<D$_o$
120.
121.
122.
123.
124.
•Steep decrease in surface energy as microdroplet makes contact and is pulled towards the cholesterol surface.
•Thermodynamics pushes the droplet towards a lower energy state, and therefore stick to and coat the arterial plaque.

FIG. 4: Force with which Microdroplet is pulled against Cholesterol
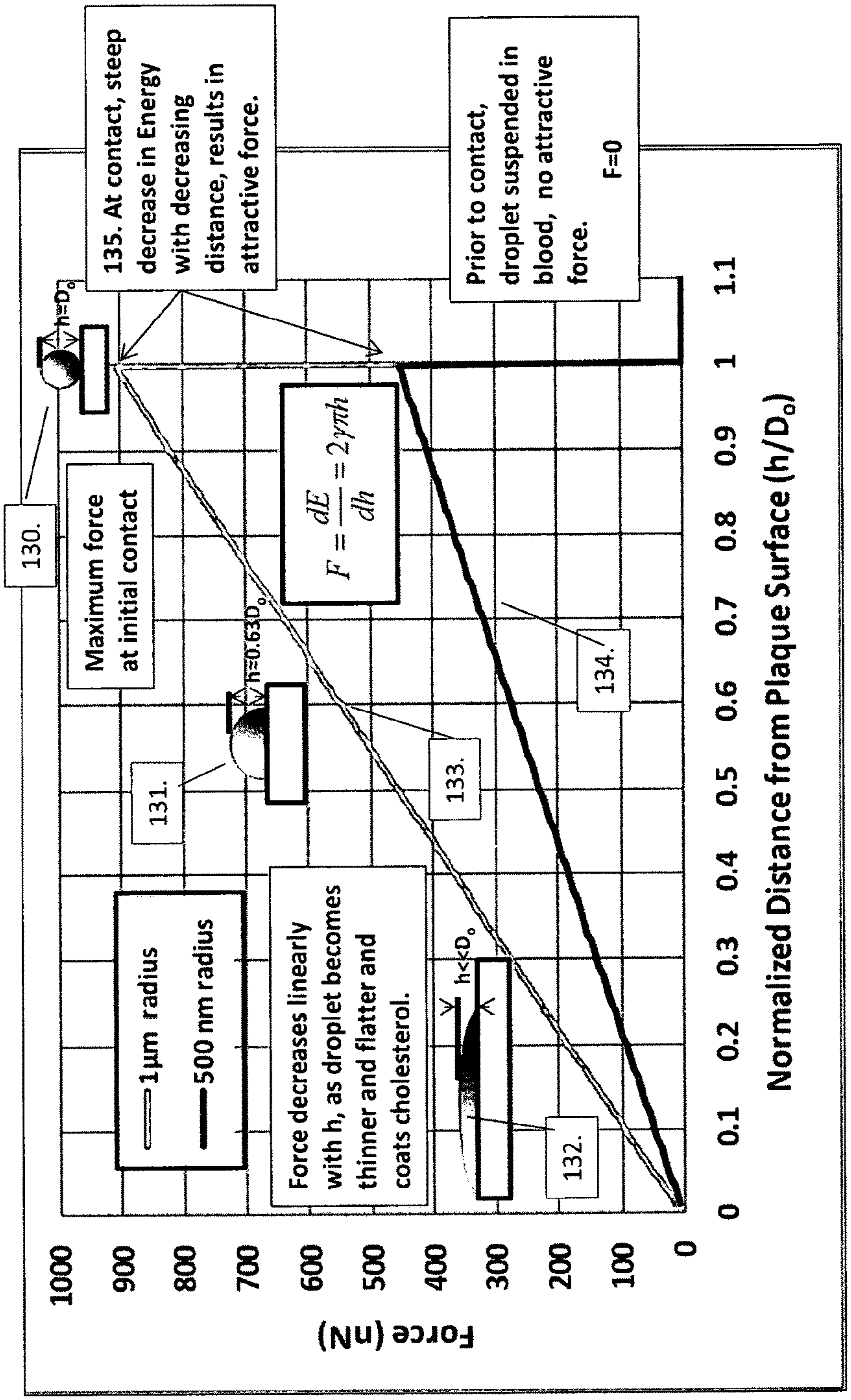
•Binding force between the microdroplets and free cholesterol is important to ensure high selectivity.
•Droplets will bind to cholesterol upon contact FIG. 5: Biocompatible Solvent Microdroplet Ultrasonic Emulsifier
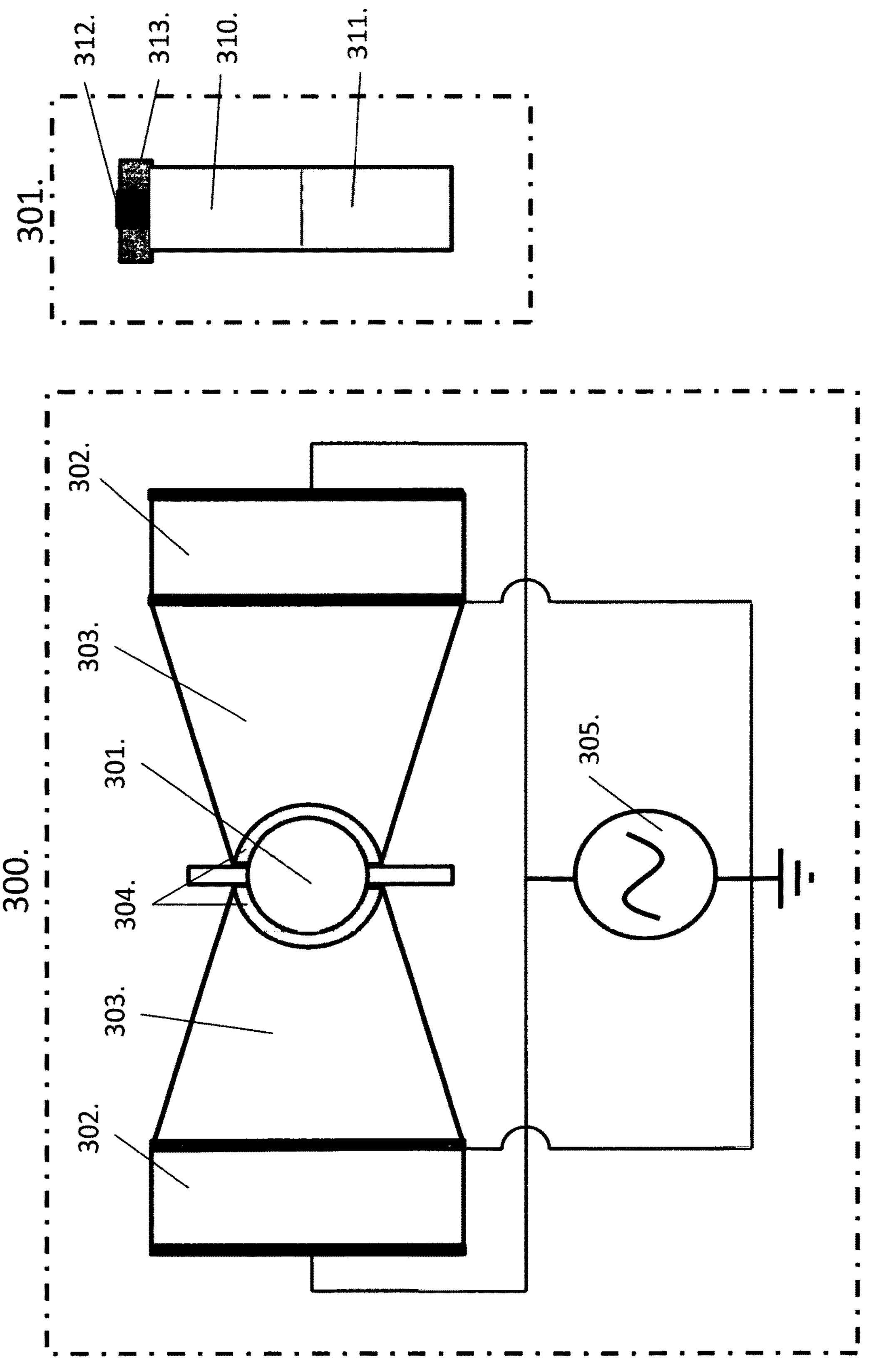

FIG. 6: Fabrication of Pharmaceutically acceptable biocompatible microdroplet solvent emulsion
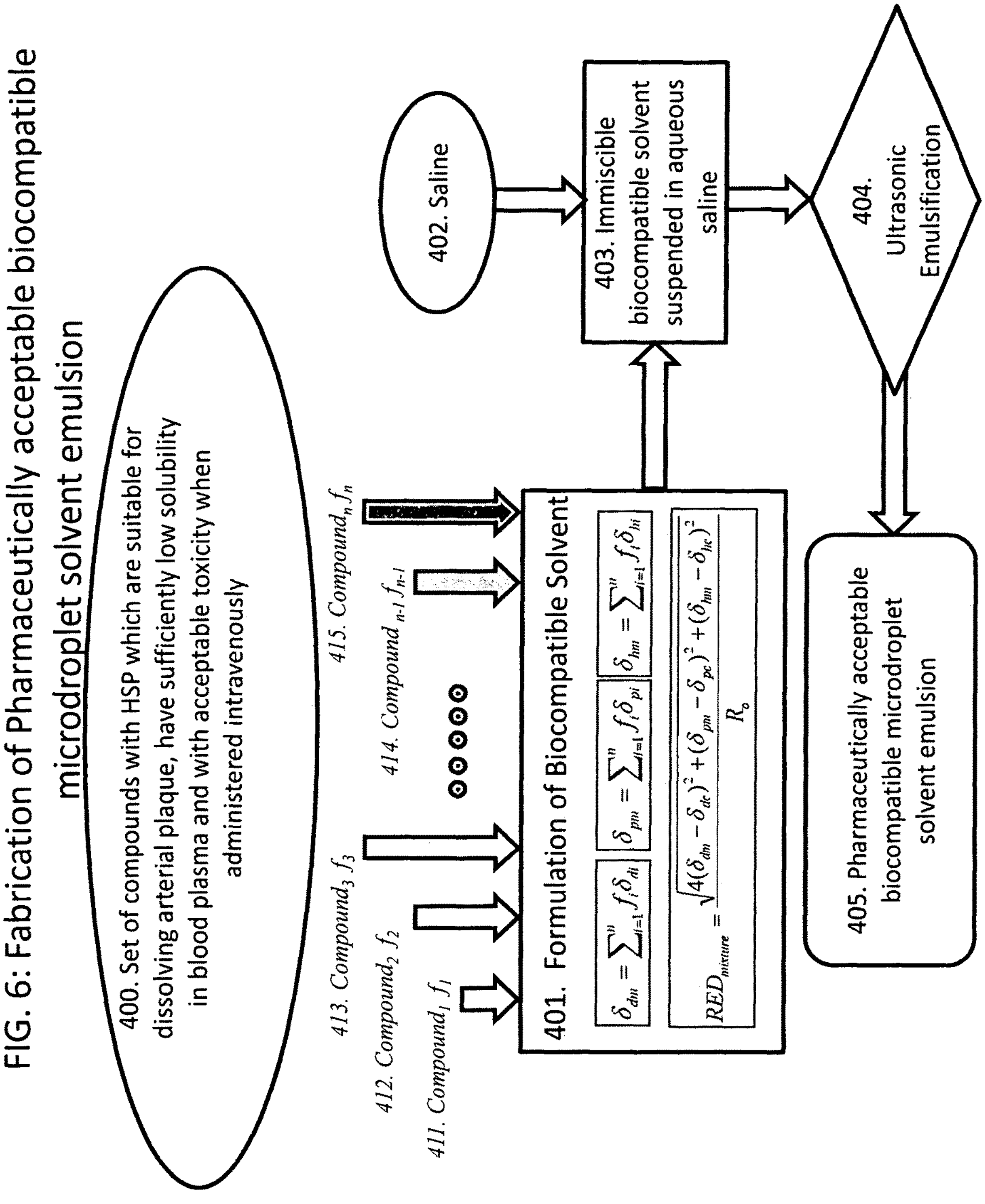

FIG. 7: Fabrication of Pharmaceutically acceptable biocompatible microdroplet solvent emulsion with very low RED

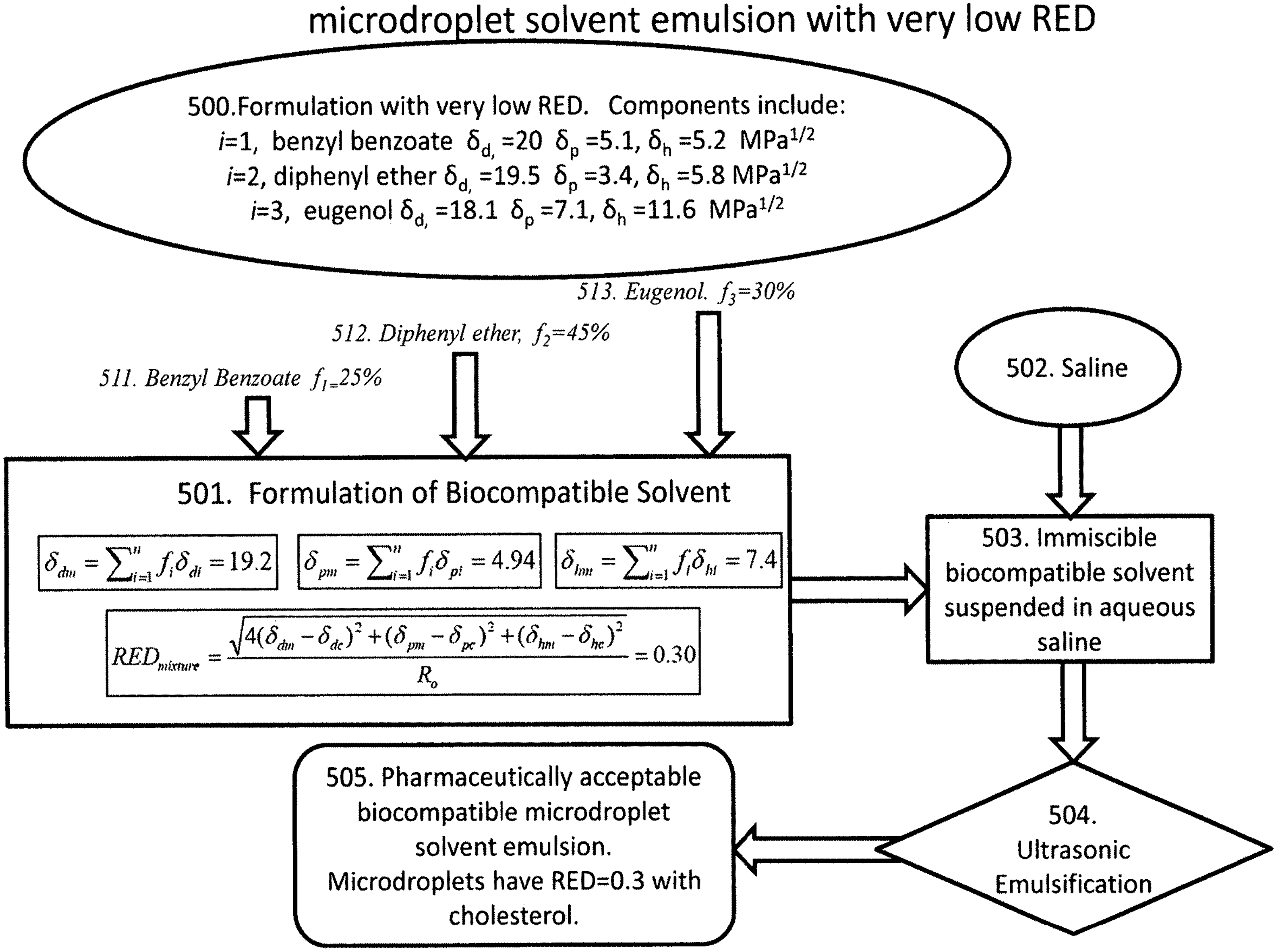

500. Formulation with very low RED. Components include:
$i=1$, benzyl benzoate $\delta_{d_1}=20$ $\delta_{p_1}=5.1$, $\delta_{h_1}=5.2$ MPa$^{1/2}$
$i=2$, diphenyl ether $\delta_{d_2}=19.5$ $\delta_{p_2}=3.4$, $\delta_{h_2}=5.8$ MPa$^{1/2}$
$i=3$, eugenol $\delta_{d_3}=18.1$ $\delta_{p_3}=7.1$, $\delta_{h_3}=11.6$ MPa$^{1/2}$

*511. Benzyl Benzoate $f_1=25\%$*

*512. Diphenyl ether; $f_2=45\%$*

*513. Eugenol. $f_3=30\%$*

**501.

FIG. 8 : Dispensing and filtration system connected to patient.
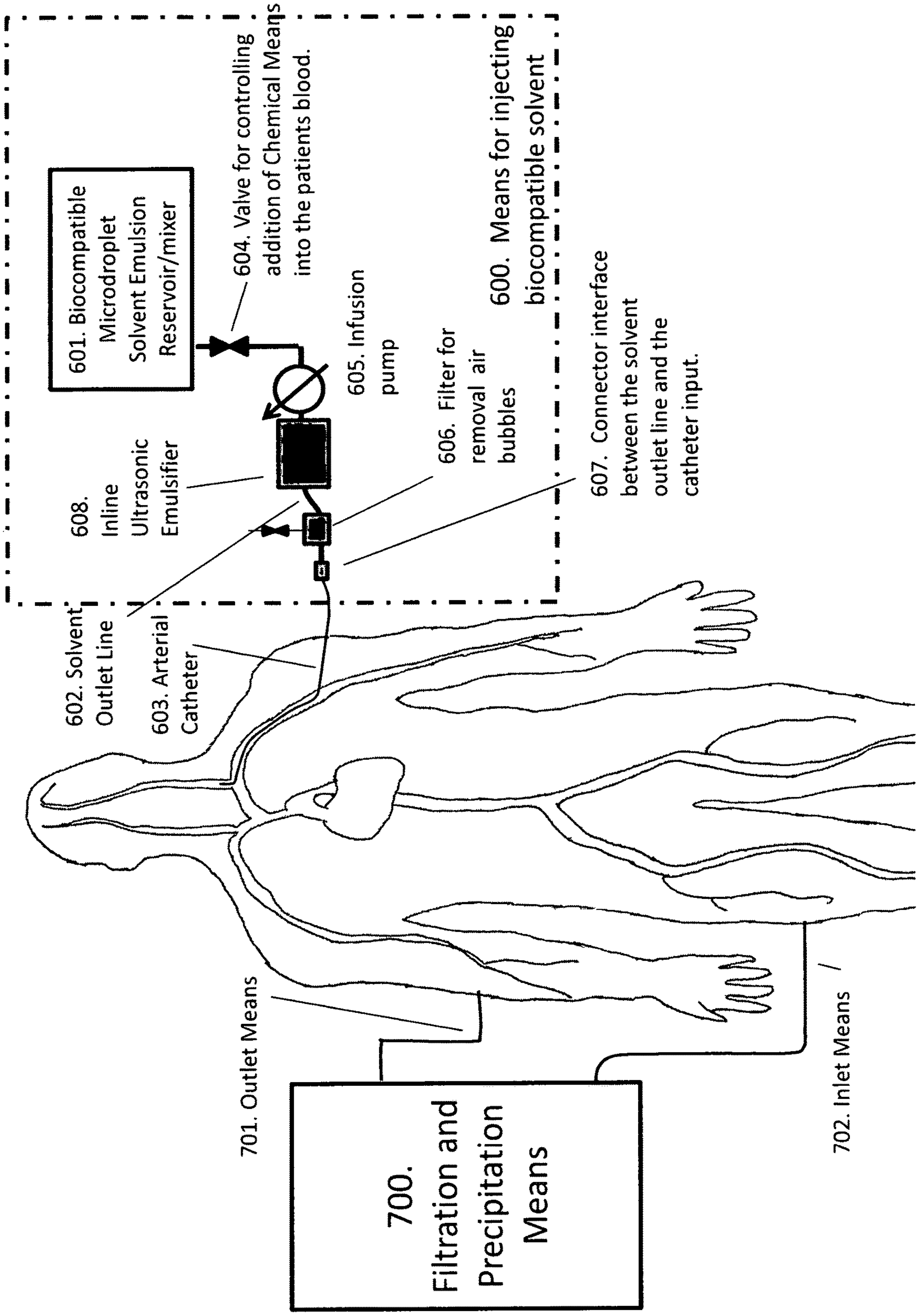

FIG. 9: Micromachined catheter tip for microdroplet generation
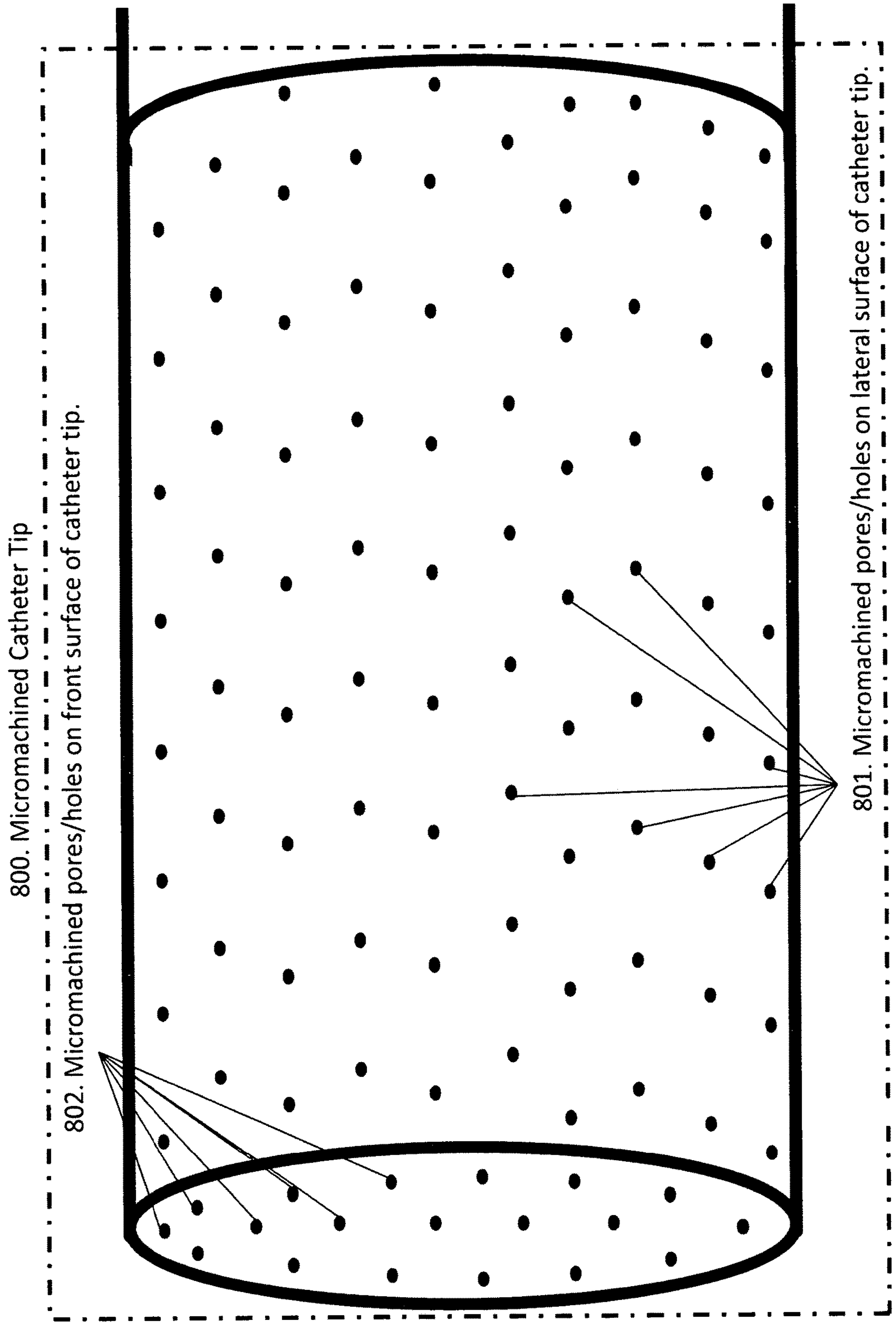

FIG. 10: Catheter with micromachined tip for intravenous microdroplet administration
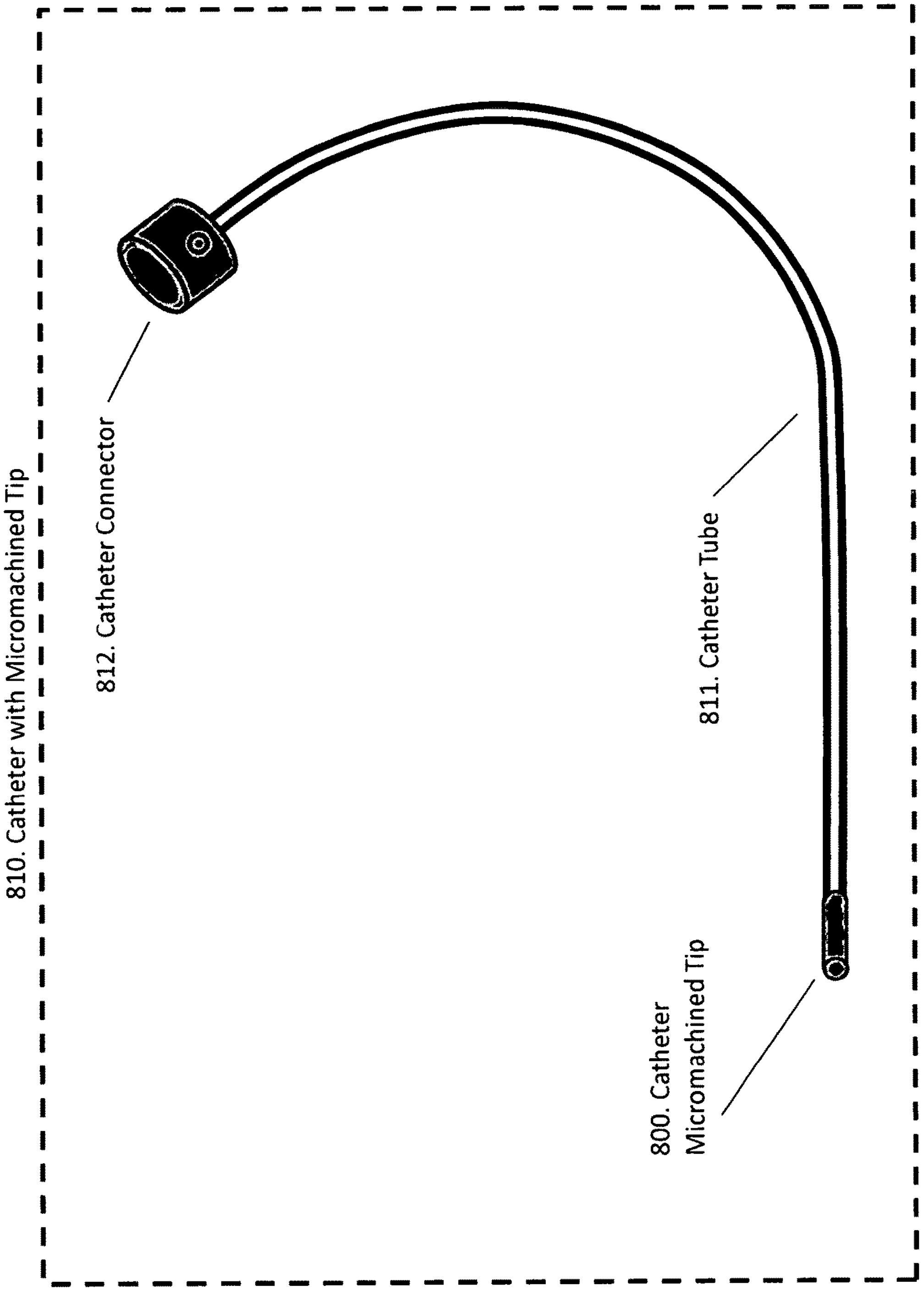

FIG. 11: Hansen Solubility Parameters of Cholesterol, water, select alcohols and fatty acids

| | Substance | CAS Number | Chem. Eq. | HSP Parameters $\delta_d$ | $\delta_p$ | $\delta_h$ | Ro | $Ra^2$ | RED |
|---|---|---|---|---|---|---|---|---|---|
| | Cholesterol | 57-88-5 | $C_{27}H_{46}O$ | 20.4 | 2.8 | 9.4 | 12.6 | | |
| | Water | | $H_2O$ | 15.5 | 16 | 42.3 | | 1353 | 2.92 |
| Alcohols | Ethanol | 64-17-8 | $C_2H_6O$ | 15.8 | 8.8 | 19.4 | | 221 | 1.18 |
| | n-Propanol | 71-23-5 | $C_3H_8O$ | 16 | 6.8 | 17.4 | | 157 | 1.00 |
| | n-Butanol | 71-36-3 | $C_4H_{10}O$ | 16 | 5.7 | 15.8 | | 127 | 0.89 |
| Fatty Acids | Oleic acid | 112-80-1 | $C_{18}H_{34}O_2$ | 16 | 2.8 | 6.3 | | 87 | 0.74 |
| | Ricinoleic acid | 141-22-0 | $C_{18}H_{34}O_3$ | 15.9 | 4.6 | 12 | | 91 | 0.76 |
| | ALA ω3 | 463-40-1 | $C_{18}H_{30}O_2$ | 18.4 | 2.66 | 4.6 | | 39 | 0.50 |
| | EPA ω3 | 10417-94-4 | $C_{20}H_{30}O_2$ | 18.5 | 3.19 | 5 | | 34 | 0.46 |
| | DHA ω3 | 6217-54-5 | $C_{22}H_{32}O_2$ | 18.5 | 3.3 | 5.1 | | 33 | 0.46 |

Table 1: Hansen Solubility Parameters of cholesterol, water, select alcohols, and fatty acids, along with their Relative Energy Difference (RED) with cholesterol. The alcohols cannot be used as the primary component of a biocompatible solvent given they are water soluble and will dissolve in the water based blood, but their HSP parameters are provided as reference.

FIG. 12: Hansen Solubility Parameters (HSP) of select monoterpene and sesquiterpene compounds

| | | | | HSP Parameters | | | | | |
|---|---|---|---|---|---|---|---|---|---|
| | Substance | CAS Number | Chem. Eq. | $\delta_d$ | $\delta_p$ | $\delta_h$ | Ro | $Ra^2$ | RED |
| Terpenes | Limonene | 138-86-3<br>5989-27-5<br>5989-54-8 | $C_{10}H_{16}$ | 17.2 | 1.8 | 4.3 | | 68 | 0.65 |
| | Terpinene | 99-86-5<br>99-84-3<br>99-85-4<br>586-62-9 | $C_{10}H_{16}$ | 17.2 | 1.8 | 4.3 | | 68 | 0.65 |
| | Dipentene | 136-86-3 | $C_{10}H_{16}$ | 16.7 | 2.2 | 4 | | 84 | 0.73 |
| | Ocimene | 502-99-9<br>3338-55-4<br>3779-61-1 | $C_{10}H_{16}$ | 16.5 | 2 | 9.1 | | 62 | 0.62 |
| | Terpinolene | 99-86-5<br>99-84-3<br>99-85-4<br>586-62-9 | $C_{10}H_{16}$ | 16.9 | 1.8 | 4.1 | | 78 | 0.70 |
| | Sylvestrene | 1461-27-4 | $C_{10}H_{16}$ | 16.6 | 3 | 4.1 | | 86 | 0.74 |
| | Phellandrene | 99-83-2<br>555-10-2 | $C_{10}H_{16}$ | 16.5 | 1.6 | 3.9 | | 93 | 0.76 |
| | Bisabolene | 17627-44-0<br>495-61-4<br>495-62-5 | $C_{15}H_{24}$ | 16.7 | 2.2 | 4 | | 84 | 0.73 |
| | Zingiberene | 495-60-3 | $C_{15}H_{24}$ | 16.6 | 1.4 | 4.1 | | 88 | 0.74 |
| | Myrcene | 123-35-3 | $C_{10}H_{16}$ | 16 | 2.2 | 5.1 | | 96 | 0.78 |

Table 2: Hansen Solubility Parameters (HSP) of select monoterpene and sesquiterpene compounds along with their Relative Energy Difference (RED) with cholesterol.

FIG. 13: Hansen Solubility Parameters of select monoterpene keytones as well as some monoterpenoids

| | Substance | CAS Number | Chem. Eq. | HSP Parameters | | | Ro | $Ra^2$ | RED |
|---|---|---|---|---|---|---|---|---|---|
| | | | | $\delta_d$ | $\delta_p$ | $\delta_h$ | | | |
| Monoterpene keytones | Carvone | 99-49-0<br>6485-40-1<br>2244-16-8 | $C_{10}H_{14}O$ | 18 | 5.6 | 6.4 | | 40 | 0.50 |
| | Acetophenone | 98-86-2 | $C_8H_8O$ | 19.6 | 8.6 | 3.7 | | 69 | 0.66 |
| | Pulegone | 89-82-7 | $C_{10}H_{16}O$ | 17.5 | 8.9 | 5.5 | | 86 | 0.74 |
| | Piperitone | 89-81-6 | $C_{10}H_{16}O$ | 17 | 6.2 | 4.5 | | 82 | 0.72 |
| | Menthone | 2216-51-5<br>89-78-1 | $C_{10}H_{18}O$ | 17 | 8.1 | 4.4 | | 99 | 0.79 |
| | Umbellulone | 24545-81-1<br>546-78-1 | $C_{10}H_{14}O$ | 17.7 | 6.6 | 4.1 | | 72 | 0.67 |
| | Artemisia Ketone | 546-49-6 | $C_{10}H_{16}O$ | 15.9 | 5.8 | 5.1 | | 108 | 0.83 |
| Monoterpenoid | Geraniol | 106-24-1 | $C_{10}H_{18}O$ | 16 | 4.7 | 11 | | 84 | 0.73 |
| | 1,8 cineole | 470-82-6 | $C_{10}H_{18}O$ | 16.7 | 4.6 | 3.4 | | 94 | 0.77 |
| | 1,4-Cineole | 470-67-7 | $C_{10}H_{18}O$ | 17.1 | 3.6 | 3.7 | | 77 | 0.70 |

Table 3: Hansen Solubility Parameters of select monoterpene keytones as well as some monoterpenoids along with their Relative Energy Difference with cholesterol.

FIG. 14: Hansen Solubility Parameters of select monoterpene and sesquinterpene alcohols, as well as diverse compounds

| | Substance | CAS Number | Chem. Eq. | HSP Parameters $\delta_d$ | $\delta_p$ | $\delta_h$ | Ro | $Ra^2$ | RED |
|---|---|---|---|---|---|---|---|---|---|
| Monoterpene and Sesquiterpene Alcohols | Terpineol | 98-55-5 | $C_{10}H_{18}O$ | 17 | 5.3 | 10.9 | | 55 | 0.59 |
| | Menthol | 2216-51-5<br>89-78-1 | $C_{10}H_{20}O$ | 16.6 | 4.7 | 10.6 | | 63 | 0.63 |
| | Nerol | 106-25-2 | $C_{10}H_{18}O$ | 16.7 | 4.5 | 11.3 | | 61 | 0.62 |
| | Citronellol | 106-22-9 | $C_{10}H_{20}O$ | 16 | 4.7 | 10.7 | | 83 | 0.72 |
| | Farnesol | 4602-84-0 | $C_{15}H_{26}O$ | 16.4 | 3.8 | 7.7 | | 68 | 0.65 |
| | Nerolidol | 7212-44-4<br>3790-78-1<br>40716-66-3 | $C_{15}H_{26}O$ | 16.4 | 2.7 | 8.7 | | 65 | 0.64 |
| Diverse | Eugenol | 97-53-0 | $C_{10}H_{12}O_2$ | 18.1 | 7.1 | 11.6 | | 44 | 0.53 |
| | Carvacrol | 499-75-2 | $C_{10}H_{14}O$ | 16.5 | 3.2 | 11.4 | | 65 | 0.64 |
| | Citral | 5392-40-5 | $C_{10}H_{16}O$ | 16.3 | 2.3 | 6.2 | | 78 | 0.70 |
| | Citronellal | 106-23-0 | $C_{10}H_{18}O$ | 16.2 | 5.9 | 5.2 | | 98 | 0.78 |
| | Perillaldehyde | 2111-75-3 | $C_{10}H_{14}O$ | 17.1 | 6.9 | 5.9 | | 73 | 0.68 |
| | Linalyl acetate | 115-95-7 | $C_{10}H_{20}O_2$ | 16 | 2.8 | 5.5 | | 93 | 0.76 |
| | Diethyl carbonate | 105-58-8 | $C_5H_{10}O_3$ | 16.6 | 3.1 | 6.1 | | 69 | 0.66 |
| | benzyl benzoate | 120-5-4 | $C_{14}H_{12}O_2$ | 20 | 5.1 | 5.2 | | 24 | 0.39 |
| | diphenyl ether | 101-84-8 | $C_{12}H_{10}O$ | 19.5 | 3.4 | 5.8 | | 17 | 0.32 |

Table 4: Hansen Solubility Parameters of select monoterpene and sesquinterpene alcohols, as well as diverse compounds.

USE OF BIOCOMPATIBLE MICRODROPLETS FOR THE TREATMENT OF ATHEROSCLEROSIS, HEART DISEASE AND STROKE

CROSS REFERENCE TO RELATED APPLICATIONS

This application is a continuation in part of U.S. patent application Ser. No. 14/608,197 filed Jan. 29, 2015, entitled "Apparatus, System and Method for the Treatment of Atherosclerosis, Heart Disease and Stroke" as well as a continuation in part of U.S. Provisional Application No. 61/975,006 filed Apr. 4, 2014, entitled "Apparatus, System and Method for the Treatment of Atherosclerosis and other Conditions Related to Fat or Lipid Accumulation in the Body" and a continuation in part of 61/932,781 filed Jan. 29, 2014, entitled "Apparatus, System and Method for the Treatment of Atherosclerosis and other Conditions Related to Fat or Lipid Accumulation in the Body" which are all incorporated herein by reference.

TECHNICAL FIELDS

The present invention generally relates to a system, method and apparatus for treating atherosclerosis by progressively reducing the build up of cholesterol and plaque from the walls of a patient's arteries. The invention will find application in treating and preventing heart disease and stroke. The invention more specifically relates to a pharmaceutically correct emulsion of biocompatible microdroplets which can be administered intravenously to safely dissolve and reverse the accumulation of atherosclerotic plaque in a patient, to reduce the risk of heart disease and stroke. Furthermore, the invention can also be used to treat small arteries to address disorders such as small vessel syndrome, cerebral small vessel disease, and coronary microvascular disease. The invention relates to both the use of a novel biocompatible microdroplet emulsion, which can be administered intravenously, and a medical device which can be used to generate the microdroplet emulsion prior to administration within the patient.

BACKGROUND

Cholesterol and fats are essential for life. However, the link between heart disease and high levels of cholesterol and fats is well established. High levels of cholesterol in blood circulation, depending on how it is transported within lipoproteins, are strongly associated with the progression of atherosclerosis. For a person of about 68 kg, their typical total body cholesterol synthesis is about 1 g per day and their total body content is about 35 g. Typical daily additional dietary intake of cholesterol in the United States is 200-300 mg. The body compensates for cholesterol intake by reducing the amount synthesized.

With a solubility of 0.000095 grams/litre at 30° C., cholesterol is only slightly soluble in water. Since cholesterol can only dissolve and travel in the water-based bloodstream at exceedingly small concentrations, it is transported through the circulatory system within lipoproteins. Lipoproteins are complex discoidal particles which have an exterior composed of amphiphilic proteins and lipids whose outward-facing surfaces are water-soluble and inward-facing surfaces are lipid-soluble. Amphipathic molecules such as phospholipids and cholesterol are transported in the monolayer surface of the lipoprotein particle.

"In addition to providing a soluble means for transporting cholesterol through the blood, lipoproteins have cell-targeting signals that direct the lipids they carry to certain tissues. For this reason, there are several types of lipoproteins within blood called, in order of increasing density, chylomicrons, very-low-density lipoprotein (VLDL), intermediate-density lipoprotein (IDL), low-density lipoprotein (LDL), and high-density lipoprotein (HDL). The more lipids and the less protein a lipoprotein has, the less dense it is. The cholesterol within all the various lipoproteins is identical. However, some cholesterol is carried as "free" alcohol and some is carried as fatty acid esters, also referred to as cholesterol esters.

The different lipoproteins contain apolipoproteins, which serve as ligands for specific receptors on cell membranes. In this way, the lipoprotein particles are molecular addresses that determine the start—and end points for cholesterol transport.

In developed countries, the availability of clean water, adequate food and advanced health care services have resulted in significantly increased life spans. However, heart disease, more specifically atherosclerosis and atheroma processes, have become an increasingly important problem and burden for society. In North America and Europe, despite substantial efforts to educate the public on risk factors and research into pharmaceutical treatments, atheroma continues to be the number one underlying basis for disability and death. Thus, increasing efforts towards better understanding, treating and preventing the problem are continuing to evolve. In addition to heart disease and stroke, atherosclerosis is also believed to be an important cause of dementia and cognitive decline in the elderly. Manifestations of atherosclerosis in small vessels of the brain are often referred to as cerebral small vessel disease, small vessel ischemic disease, white matter disease, periventricular white matter changes, perivascular chronic ischemic white matter disease of aging, white matter hyperintensities, age-related white matter changes and leukoaraiosis. Increasing research based evidence is showing a very strong correlation between atherosclerosis and narrowing of blood vessels in the brain with Alzheimers. When the small arteries of the heart are impaired due to atherosclerosis, this condition is known as coronary microvascular disease (MVD). Coronary MVD as well as cerebral small vessel disease cannot be treated using angioplasty given the small size and large number of arteries affected.

DISCLOSURE OF INVENTION

The current invention comprises of a pharmacologically acceptable microdroplet emulsion, which selectively targets and dissolves atherosclerotic plaque when administered intravenously to help treat and bring about a systematic reversal of atherosclerosis in a patient. The microdroplets will have solubility parameters which are well matched to those of cholesterol, and will preferentially bind to cholesterol, cholesterol esters or other fatty material in arterial plaque to facilitate the dissolution of the arterial plaque. The biocompatible microdroplet emulsion can be used in small repeated doses to bring about a gradual reduction of atherosclerosis, thereby reducing the risk of heart disease, stroke or other conditions which result from the narrowing of arterial blood vessels. Furthermore, the microdroplets will comprise of a biocompatible compound, or mixture of compounds, which can be safely metabolized or eliminated by the patient after the microdroplets have been circulating through the cardiovascular system for some time. It takes blood approximately 1 minute to make a loop through the cardiovascular system. As such, even if the microdroplets are injected in a vein, or muscle tissue, within about 1 minute, the microdroplets will circulate back to the arterial system and have the opportunity to make contact with the atherosclerotic plaque in a patient's arteries. In situations where a more aggressive, urgent treatment is necessary, a larger dose of microdroplets can be used, in conjunction with a medical device which can filter the microdroplets after they have circulated through the cardiovascular system. The microdroplets will have a diameter which is sufficiently small to circulate through the cardiovascular system and allow easy passage through the capillaries without causing blood clots, embolisms or an impediment to blood flow. An average red blood cell has a diameter of about 7 microns (micron=$10^{-6}$ meters) and an average capillary has a mean diameter of about 8 microns. Red blood cells actually deform slightly and pass single file through the smallest capillaries. Research on nano-devices such as microspheres suggests that rigid structures such as nanobots must have a diameter of less than 4 microns to pass unimpeded through the cardiovascular system. As such, microdroplets with a diameter of about 4 microns or less, should easily circulate through the cardiovascular system without being trapped in capillaries and disrupting circulation. For the purpose of this invention, the term microdroplet will generally refer to a droplet that can be safely injected in the cardiovascular system with an acceptably low probability of being trapped in a capillary. More specifically, the term microdroplet will refer to a droplet with diameters ranging from approximately 10 microns to a fraction of a nanometer in diameter, ideally the maximum size should be 4 microns or less to reduce the probability that a microdroplet get trapped in a capillary and block blood flow through this capillary.

The composition of arterial plaque can vary. An atherosclerotic lesion will initially appear as an exposed fatty streak along the wall of an artery. The fatty streaks will gradually thicken over the course of many years or decades. After some time, typically 3 to 4 decades, the plaque, may be covered by a layer of endothelial cells and/or fibrous tissue and may have grown enough to substantially reduce the cross section of an artery. Despite having reduced the cross section of the artery, usually plaque which is covered by fibrous tissue and endothelial cells do not pose an imminent risk of heart attack or stroke. However, exposed plaque, where the hard cholesterol surface is directly exposed to circulating arterial blood poses a greater risk. The arterial plaque may comprise of undesirable fatty compounds such as cholesterol, cholesterol esters, fat, endothelial cells, fibrous tissue and other materials which may build up along the walls of diseased arteries. Given that the cholesterol, cholesterol esters, and fatty compounds which make up a majority of the plaque are hydrophobic compounds with vastly different solubility parameters than other surfaces within the cardiovascular system, the microdroplets can be designed to preferentially bind to these undesirable compounds.

Given that a relatively small quantity of biocompatible microdroplet solvent emulsion will be injected into the cardiovascular system with each dose, combined with the large surface area of arteries, veins and capillaries which make up the cardiovascular system, it is important that the microdroplets preferentially attach to free cholesterol or fatty streaks on the surface of arteries, as opposed to other surfaces. This can be achieved by designing the microdroplets to have a low surface energy density interface when attaching to arterial plaque, and a high surface energy density when coming into contact with other surfaces such as the endothelial cells lining blood vessels, or the outer membrane of blood cells, causing the microdroplets to preferentially bind to arterial plaque and dissolve cholesterol as they seek to minimize their surface energy. The microdroplets should have solubility parameters which are a good match to the compounds which make up the plaque. Furthermore, the surface energy density between the microdroplet and arterial plaque should be sufficiently low that the microdroplets will preferentially attach to arterial plaque, as opposed to other surfaces within the cardiovascular system, and provide a high level of selectivity. Other surfaces in the cardiovascular system are hydrophilic. All cells have an outer membrane which is comprised of a phospholipid bilayer. The phospholipid bilayer is oriented such that phospholipid molecules have their polar hydrophilic head oriented outwards towards extracellular space, and the inner layer is arranged such that the hydrophobic head is oriented inwards, towards the cytoplasm on the interior of the cell. This ensures that the cell is covered with polar heads and has a low surface energy with water or blood plasma. Healthy blood vessels are covered by endothelial cells, which will also present a hydrophilic surface on the outer surface of its membrane. This is also true for blood cells or any other living cells within the human body.

Similarly, blood proteins such as human albumin, chylomicrons, VLDL, LDL and HDL are dissolved in blood plasma and are therefore predominantly covered by polar heads to offer a low surface energy density with water. A few zones which are non polar, known as binding sites, enable proteins to transport water insoluble molecules such as long chain or very long chain fatty acids as well as cholesterol and other water insoluble lipids. However, these binding sites make up a relatively small fraction of the total surface area of the protein molecule.

Another requirement is that the microdroplets must not dissolve appreciably in the blood. An adult human can have 4 to 5 litres of blood, whereas a few ml of biocompatible microdroplet solvent emulsion will be administered per dose. To ensure that the microdroplets travel as discrete microdroplets through the cardiovascular system and make contact with the atherosclerotic plaque, it is important that they do not dissolve within the blood rapidly. As such, compounds which have a good solubility match to cholesterol but have relatively good (such as an alcohol) or even modest (short and medium chain fatty acids) solubility in the water based blood plasma are not good candidates from which to design the microdroplet emulsion. Compounds which have very poor solubility within the water based blood plasma such as long or very long chain fatty acids and biocompatible hydrocarbons are better candidates.

The biocompatible microdroplet solvent means can preferably comprise of any compound or mixture of compounds which are reasonably insoluble in water or blood, and which are known to have the ability to dissolve arterial plaque, cholesterol, cholesterol esters or other fatty compounds within the plaque. To effectively dissolve arterial plaque in-vivo it is very important that the biocompatible solvent be sufficiently insoluble in blood to allow a small discrete microdroplet to travel through the blood stream, from the injection point, to the plaque which is being treated. If the biocompatible solvent dissolves within the blood, such as an alcohol, the solubility parameters of the resultant mixture will be very nearly identical to that of blood and will not dissolve cholesterol or arterial plaque. Conversely, if a discrete microdroplet of the biocompatible solvent makes contact with the plaque, then the cholesterol molecule in the plaque will be surrounded by multiple molecules of the biocompatible solvent, which have similar solubility parameters as the cholesterol, and the cholesterol will be drawn away from the plaque and into the droplet. Some of the water insoluble solvents which have been tested and are showing very promising results include long chain and very long chain fatty acids such as Alpha-linolenic acid, Linoleic acid, oleic acid, Elcosapentaenoic acid, Docosahexaenoic Acid, capric acid (a medium chain saturated fatty acid common in plant and animal milk), 1,4-dioxane, and some brominated vegetable oils such as 1-Bromonaphthalene. Terpenes, terpenoids as well as cyclic hydrocarbons which are found in foods but especially herbs and spices, have also showed extremely good efficacy at dissolving cholesterol in whole blood. A few examples of compounds which have shown excellent results include 1,8 cineole, terpinene, carvone, eugenol, diethyl carbonate, terpeneol, carvacrol, eugenol, benzyl benzoate and diphenyl ether. A complete list of the compounds being studied and tested can be found in table 1, table 2, table 3 and table 4. An organic salt, Esters, an organo-metallic compound could also be used as the main component or an addition to the biocompatible microdroplet solvent means. Essentially any organic molecule which can be administered intravenously with acceptable side effects, is sufficiently insoluble in blood to travel as a discrete microdroplet without being dissolved prior to reaching arterial plaque and which is capable of dissolving cholesterol, cholesterol esters or other materials within the arterial plaque, could potentially be used.

Use of amphipathic molecules or surfactants such as lecithin or similar molecules, which reduce the surface tension at the microdroplet/blood interface is not preferred and will hinder the performance of the biocompatible microdroplet solvent emulsion. To ensure the microdroplets bind with the cholesterol in arterial plaque, the microdroplet must have a low surface energy density when making contact with plaque. A surfactant would form micelles at the microdroplet/blood interface with the hydrophilic tails facing outwards, and will lower the surface energy density of the microdroplet with blood, thereby decreasing the selectivity of the microdroplet to cholesterol. Furthermore, the surfactant would also decrease the surface energy density of the microdroplets with the phospholipid bilayer of cell membranes, and would facilitate the absorption of the lipid compounds within the microdroplets, into cells, as opposed to binding and dissolving arterial plaque. For most microdroplet emulsions within the chemical and pharmaceutical industry, a surfactant is used to make the emulsion thermodynamically stable, and prevent the microdroplets from coalescing. Furthermore, when a microdroplet emulsion is used for drug delivery, the surfactant molecule is beneficial since it allows the microdroplet to come into contact with the cell membrane, and help facilitate absorption of the drug into the cell. However, for the purpose of this invention, the microdroplets must form a less stable emulsion, where the microdroplets have a high surface energy density at the microdroplet/blood interface or when bumping into cell membranes and a low surface energy density when the microdroplets make contact with free cholesterol or cholesterol esters in arterial plaque. Use of an emulsifying molecule or surfactant would work against this objective by reduce the surface energy density at the microdroplet/aqueous interface and increase the surface energy density at the microdroplet/cholesterol interface. A list of common surfactants which are commonly used to stabilize microemulsions includes Polysorbates (Tween™), Sodium dodecyl sulfate (sodium lauryl sulfate), Lauryl dimethyl amine oxide, Cetyltrimethylammonium bromide (CTAB), Polyethoxylated alcohols, Polyoxyethylene sorbitan, Octoxynol (Triton X100™), N,N-dimethyldodecylamine-N-oxide, Hexadecyltrimethylammonium bromide (HTAB), Polyoxyl 10 lauryl ether, Brij 721™, Bile salts (sodium deoxycholate, sodium cholate), Polyoxyl castor oil (Cremophor™), Nonylphenol ethoxylate (Tergitol™), Cyclodextrins, Lecithin, and Methylbenzethonium chloride (Hyamine™). This list is by no means complete and other surfactants exist which have not been listed here.

As opposed to using a single compound, the microdroplets can comprise of a combination of several different compounds which are broken down via different metabolic pathways to reduce potential toxic side effects for a given quantity of biocompatible microdroplet solvent, compared to the same quantity of a single compound. Furthermore, given that the solubility parameters of a solution is equal to the weighted average of the Hansen solubility parameters of the individual components, it is possible to mix 2 or more compounds together to arrive at a solvent which is better suited to dissolving cholesterol, or other components of arterial plaque, than any of the components alone. These two factors can be used advantageously to develop a biocompatible microdroplet solvent which is both more effective and less toxic.

Given that many of the potential components of the microdroplet biocompatible solvent means which have been named above are actually contained in common foods and oils, it is important to review blood chemistry as well as the method in which lipids are absorbed and carried within the body to properly understand the invention being disclosed herein. For example, Alpha-linolenic acid (ALA Omega 3), Linoleic acid (an Omega 6), oleic acid (an Omega 9), Eicosapentaenoic acid (EPA Omega3), Docosahexaenoic Acid (DHA Omega 3) are contained in common foods and are very safe for human consumption, and many of these molecules have even been shown to be beneficial in preventing heart disease. These molecules are generally known as fatty acids, and more specifically long chain fatty acids since they all contain between 12 and 22 carbon atoms. Although we consume these fatty acids in everyday food, similarly to cholesterol, they are insoluble in water and as such cannot travel within the water based blood stream as free fatty acids but must be transported within lipoproteins. The same can be said of many organic hydrocarbons which are found in herbs and spices and give these foods their characteristic taste and smell, such as eugenol, carvacrol, limonene, 1,8 cineole, carvone, acetophenone, terpineol and other compounds listed in tables 1, 2, 3 and 4. Although these compounds are not actually fatty acids, they are often classified as lipids given they are water insoluble. For the purpose of the description of the digestive process below, all these water insoluble compounds listed in table 1 will be loosely referred to as lipids, with the exception of water, ethanol, propanol and butanol in table 1.

Dietary fatty-acids and more generally lipids are absorbed differently depending on the size of the molecule and the extent to which they dissolve in the water based blood. As food is digested within the intestine and fatty acids and lipids are released from the food, the fatty acids will dissolve through the lining of the intestine. Short and medium chain fatty acids (2-10 carbon atoms) and other lipids which are moderately water soluble are absorbed directly into the blood of the stomach lining and travel through the portal vein towards the liver where they are processed. The portal vein is not a true vein since it does not carry blood back towards the heart but is a dedicated blood vessel which carries nutrient rich blood directly from the gastrointestinal lining back to the liver. Lipids which are not water soluble are absorbed differently. Given the importance of fatty acids to human nutrition, the absorption of long chain and very long chain fatty acids has been studied in detail. Long Chain fatty acids (12-22 carbon atoms) and Very Long Chain fatty acids (greater than 22 carbon atoms) are not soluble in the blood and therefore cannot be transported directly in the portal vein. The body has developed a fairly complex process to absorb and carry these long chain fatty acids. Given that they cannot be carried in the blood due to their insolubility, they are instead assembled into triglycerides and combined with protein to create a chylomicron directly within the villi of the intestinal wall. The chylomicron is a lipoprotein which originates directly within the lining of the intestine for the purpose of carrying the long chain fatty acids or other water insoluble lipids. Similarly, very low density lipoproteins (VLDL) are also produced in the intestinal wall and used to transport very long chain fatty acids. The chylomicrons and VLDL's are then transported from the intestine through the lymphatic system and enter the cardiovascular system through the thoracic duct which drains into the subclavian vein. From there, the chylomicrons travel through the cardiovascular system and can be absorbed in various tissue such as adipose tissue, or are eventually processed by the liver. Long and very long chain fatty acids which are stored in the liver, can be combined into Very Low Density Lipoproteins (VLDL), or Low Density Lipoproteins (LDL) and carried back out from the liver to other parts of the body such as adipose tissue. Some fatty acids may be released into the blood stream by adipose cells at which point albumin, a blood protein, will collect the fatty acids and carry them back to the liver. Albumin is a blood protein whose surface is mostly water soluble and as such is dissolved within the blood, but has a few hydrophobic receptor sites to which water insoluble fatty acids can bind.

It is interesting to note that although the human body needs and uses sizable quantities of water insoluble lipids such as long chain fatty acids and very long chain fatty acids, given they are not water soluble they are almost always carried about by lipoproteins. Therefore, microdroplets of fatty acid will never come into direct contact with atherosclerotic plaque in an individual's arteries. In the invention being disclosed here, fatty acids and/or other water insoluble compounds are being used as a component in the biocompatible microdroplet solvent means and these compounds are being injected intravenously directly into a patient's blood stream such that they make contact with arterial plaque. Microdroplets which make contact with atherosclerotic plaque dissolve a small quantity of cholesterol or other fatty compound from the plaque and thereby contribute to the reversal and reduction of arterial plaque.

If the biocompatible microdroplet solvent means is used without the medical device, the emulsion can be directly injected into a vein or artery, or any injection site which is sufficiently well perfused by capillaries. If a patient is known to have an artery which needs to be treated, a more focused treatment can be administered by inserting a catheter upstream of the artery which needs to be treated, and injecting the biocompatible microdroplet solvent emulsion means slightly upstream of the plaque being treated. Microdroplets of the biocompatible solvent means will then make contact with the plaque as they flow through the artery and dissolve small quantities of cholesterol and other fatty materials from the plaque. As the droplets travel downstream, they carry away the dissolved cholesterol from the area being treated. The microdroplet will eventually be pushed through the capillaries and make its ways towards the venous system. The microdroplet will gradually dissolve into the blood stream, at which point individual lipid molecules which have dissolved from the droplet will bind to albumin or other lipoproteins and be metabolized. The minute quantity of the cholesterol which had been dissolved within the droplet will also be absorbed by the albumin or other lipoproteins and be carried back to the liver or reabsorbed into other cells. The microdroplet solvent will have contributed to the reverse transport of cholesterol from arterial walls back towards the liver. If sufficiently large quantities of the biocompatible solvent means are used, all available receptor sites of the albumin may be used up at which point the droplets will continue to travel through the cardiovascular system as discrete microdroplets. If excessive amounts of the biocompatible solvent are administered during treatment, it may be beneficial to administer an injection of human albumin to the patient.

The composition of blood should also be discussed and understood in order to properly consider the operation of the filtration and precipitation means within the medical device. Blood is typically categorized into 2 main parts, 55% blood plasma and 45% blood cells. Blood plasma is composed primarily of water (92% by volume) along with 6-8% of dissolved blood proteins (albumin, VLDL, LDL, HDL, etc), iron, glucose, clotting factors, electrolytes ($Na^+$, $Ca^{2+}$, $Mg^{2+}$, $HCO_3^-$, $Cl^-$, etc.), hormones, and carbon dioxide. Blood cells are actual formed entities which include red blood cells, white blood cells and platelets. Blood cells are not dissolved in the blood but rather in suspension. This contrasts with the blood proteins and minerals which are actually soluble in the blood plasma and are therefore dissolved. For the purpose of this invention it is important to note that although some of the lipoproteins such as the chylomicrons, VLDL and LDL have low densities, they are dissolved within the blood and as such will not be separated from the blood based on their densities. Blood cells are discrete objects which are in suspension within the blood and could potentially be separated from blood based on their higher densities, however they have a higher density that water and are denser than the fatty acids being proposed as the biocompatible solvent means. In general, the average density of whole blood is approximately 1.06 $g/cm^3$, while the average density for blood cells is approximately 1.125 $g/cm^3$. Blood plasma has a slightly lower density of approximately 1.025 $g/cm^3$. A typical blood cell has a diameter of about 7 microns, whereas blood proteins and lipoproteins are considerably smaller and range in size from 1 nanometers to 100 nanometers.

Given that arterial plaque, cholesterol, cholesterol esters and other fatty compounds have a very low solubility in water, or blood, the biocompatible microdroplet solvent means is required to dissolve the fatty compounds we are targeting and allow them to be transported through the cardiovascular system and be solubilised by blood proteins and eventually metabolized. Solubility parameters can be used to predict or estimate how well a potential water insoluble solvent will dissolve the target material.

Solubility theory is a very large and complex field and one of the best and most widely accepted theories was developed by Charles Hansen in 1969. The Hansen solubility theory defines three parameters which are known as the HSP values for a compound. The HSP values quantify intermolecular forces by considering three distinct Van der Wall forces for a compound, specifically: London Dispersion Forces $\delta_d$, Keesom Polarity Forces $\delta_p$ (between permanent dipoles), and Hydrogen Bonding $\delta_h$. Molecules which have strong permanent dipoles (polar molecules) will have a fairly large $\delta_p$ parameter. Hydrogen bonding is a very strong form of polar bonding which occurs between a hydrogen atom and either a nitrogen, oxygen or fluorine atom with very high electron affinity. Water, $H_2O$, the main component of blood, has a very strong parameter for polar and hydrogen bonding given it is a polar molecule with hydrogen and oxygen atoms. Most undesirable fatty compounds tend to have very small coefficients of $\delta_h$ and $\delta_p$ and are therefore insoluble in water or blood.

The extent to which two compounds will dissolve each other can be quantified using the equations developed by Hansen:

$$(Ra)^2=4(\delta_{d2}-\delta_{d1})^2+(\delta_{p2}-\delta_{p1})^2+(\delta_{h2}-\delta_{h1})^2 \quad \text{Eq. (1)}$$

$$\text{RED}=R_a/R_o \quad \text{Eq. (2)}$$

Equation 1 calculates the relative magnitude difference of the three Hansen parameters of the two compounds to arrive at $R_a$. The smaller the value of $R_a$, the better the two compounds will dissolve each other. Equation 2 allows one to calculate the Relative Energy Difference (RED) of the solvent and the material we are trying to dissolve, by dividing $R_a$ by $R_o$. $R_a$ was calculated in Equation 1 and measures the magnitude of the difference of the HSP values of the two compounds. The units for the HSP parameters $\delta_d$, $\delta_p$, $\delta_h$ are $MPa^{1/2}$. $R_o$ is the interaction radius over which the compound we desire to dissolve has been shown to interact with potential solvents. The Relative Energy Difference (RED) is a dimensionless number which quantifies how well a solvent will dissolve a solute. For an RED>>1 the compounds will not dissolve. For an RED~1, there will be some dissolution. For an RED<1 there will be a considerable amount of dissolution. Essentially, the smaller RED value, the more solute will dissolve into the solvent, with RED=1 being a threshold where a given solute is starting to be soluble in a given solvent.

Tables 1 provides the Hansen solubility parameters for a few select biocompatible solvents which occur naturally in food as well as the HSP parameters of water. As can be seen, water which is the main component of blood has very strong polar bonding and hydrogen bonding components, and the RED value with both fat and cholesterol is considerably larger than 1, which explains why cholesterol and fat are insoluble in water. We then provide the HSP parameters for 3 alcohols which are known to be safe for human consumption is small quantities, namely Ethanol, Propanol and Butanol. The RED values for cholesterol with each of Ethanol, Propanol and Butanol is 1.32, 1.10 and 0.944 respectively. The mass fraction of cholesterol which will dissolve in a pure solution of each of these alcohols at 37° C. is 3.3%, 11% and 11.8% respectively[2]. As can be seen, smaller RED values leads to greater solubility's and it is therefore desirable that the microdroplets have a small RED value with cholesterol. For cholesterol in water the RED value is 2.9 and the mass fraction of cholesterol which will dissolve in pure water is 0.0000095% which is very negligible. One of the complications of using a water soluble solvent such as the alcohols mentioned above, is that they will mix with water. If one mixes two solvents together, the resultant HSP parameters of the solution are the weighted average of the HSP of the individual components. Since the concentration of alcohol which can safely be in a patient's blood is below 1%, the HSP of the blood/alcohol solution will be very similar to that of the blood without the alcohol. Conversely, using microdroplets of a biocompatible solvent which is "water insoluble" allows microdroplets of the solvent to travel through the blood stream, and these microdroplets have HSP parameters which are very well matched to the cholesterol or undesirable fatty compound we want to remove from the patient, and will dissolve the target material on contact. The droplets will then carry the dissolved cholesterol, cholesterol esters or other undesirable fatty compounds which have been removed from the arterial plaque, through the blood stream and will eventually be broken down and metabolized along with the dissolved cholesterol.

Many compounds which are found in food, which are both water insoluble and have an excellent solubility match to cholesterol, could be used as one of the components of the biocompatible microdroplets. These compounds are listed in tables 1, 2, 3 and 4.

Limonene, $C_{10}H_{16}$ for instance, is the primary component of lemon oil, which gives a strong citrus scent. Limonene is a colorless liquid hydrocarbon classified as a cyclic terpene. The Hansen Solubility properties for Limonene are $\delta_d$=17.2 $\delta_p$=1.8 $\delta_h$=4.3 $MPa^{1/2}$ and the Relative Energy Difference with Cholesterol is RED=0.65, which make it a very good solvent of cholesterol or arterial plaque. Furthermore, given it is a pure hydrocarbon, and non polar, it is almost completely insoluble in the water based blood plasma which will allow small microdroplets to travel through the cardiovascular system without dissolving into the water based blood plasma prior to reaching the atherosclerotic plaque. Although limonene microdroplets dissolved cholesterol in a dilute solution in water, when experiments were repeated in whole blood, the cholesterol sample seemed to accumulate precipitate and swell. Limonene was unique in this respect. Other biocompatible solvents tested and listed below did not demonstrate this phenomenon. The author repeated the experiment several times with pure limonene as well as concentrated lemon oil extract from a different source and observed the same results.

Another promising compound is 1,8-cineole, which is the primary component of eucalyptus oil. 1,8-cineole is classified as a cyclic ether and a monoterpenoid. The Hansen Solubility Parameters for 1,8-cineole are $\delta_d$=16.7 $\delta_p$=4.6 $\delta_h$=3.4 $MPa^{1/2}$ and the relative energy difference with cholesterol is only RED=0.77, making it a good solvent for arterial plaque. Microdroplets of 1,8-cineole demonstrated extremely good efficacy in whole blood. Furthermore, the efficacy of the 1,8 cineole does not seem to be degraded by the presence of larger quantities of blood, which implies there is little to no interaction between the 1,8 cineole microdroplets and components of blood. The efficacy of 1,8 cineole at dissolving cholesterol was identical to within measurement error, when comparing two experiments with up to a 4× difference in blood volume. Microdroplets of 1,8 cineole or eucalyptus oil (with approximately 80% 1,8-cineole) demonstrated excellent efficacy in whole blood.

Carvone is a naturally occurring terpenoid found in the oils of caraway seeds, spearmint and dill. The Hansen Solubility parameters of carvone are $\delta_d$=18 $\delta_p$=5.6 $\delta_h$=6.4 $MPa^{1/2}$ and it has a very small Relative Energy Difference with cholesterol of only 0.5 making it an excellent solvent of cholesterol.

Terpineol is a naturally occurring monoterpene alcohol found in several foods and herbs. The Hansen Solubility Parameters of terpineol are $\delta_d$=17 $\delta_p$=5.3 $\delta_h$=10.9 $MPa^{1/2}$. The RED with cholesterol is 0.59 making it a good solvent of arterial plaque. Given terpeneol is an alcohol, with an OH group, it has a relatively high hydrogen bonding ($\delta_h$) coefficient and as such is slightly soluble in water. It would therefore not be a good candidate as the primary component of the micro-droplet, but can be used with other compounds to adjust the HSP parameters of the mixture slightly.

Carvacrol is a monoterpenoid phenol, which gives oregano its characteristic odour, and is the primary component of oregano oil. The Hansen Solubility Parameters for carvacrol are $\delta_d$=16.5 $\delta_p$=3.2 $\delta_h$=11.4 $MPa^{1/2}$. Carvacrol is insoluble in water and can therefore travel through the blood stream as microdroplets without being dissolved in blood plasma. The Relative Energy Difference with Cholesterol is only 0.64 making it a good solvent of arterial plaque.

Menthol is an alcohol found in mint oil. The HSP parameters are $\delta_d$=16.6 $\delta_p$=4.7 $\delta_h$=10.6 $MPa^{1/2}$, and it's RED value with cholesterol is only 0.63 making it a good solvent of arterial plaque.

Eugenol is a member of the phenylpropanoids class of chemicals, and the primary component of clove oil. The HSP parameters of eugenol are $\delta_d$=18.1 $\delta_p$=7.1 $\delta_h$=11.6 $MPa^{1/2}$ and its RED value with cholesterol is only 0.53, making it a good solvent for arterial plaque.

Acetophenone, is a naturally occurring compound, and the simplest of the aromatic keytones. This chemical gives certain fruits such as apples and strawberries their fruity taste, and is used as an additive in bubble gums for this purpose. The HSP parameters for acetophenone are $\delta_d$=19.6 $\delta_p$=8.6 $\delta_h$=3.7 $MPa^{1/2}$ and its RED with cholesterol is only 0.66 making it a good solvent of atherosclerotic plaque. However, acetophenone is somewhat soluble in water and is also classified as a hypnotic drug if used in large quantities, and would therefore not be suitable as the primary component of the microdroplet, but could be used as an additive to adjust the HSP parameters of the solution. Given it has an aromatic ring, it has a very large dispersion coefficient of 19.6 $MPa^{1/2}$.

Myrcene is a naturally occurring hydrocarbon from the alkene family. The HSP parameters of myrcene are $\delta_d$=16 $\delta_p$=2.2 $\delta_h$=5.1 $MPa^{1/2}$ and the RED with cholesterol is 0.78 making it a good solvent of arterial plaque.

Ocimene is a naturally occurring hydrocarbon, a member of the monoterpene family, found in many fruits. The HSP parameters for ocimene are $\delta_d$=16.5 $\delta_p$=2 $\delta_h$=9.1 $MPa^{1/2}$ and has an RED of 0.62 with cholesterol. Ocimene is solid until about 50° C. and could not be the primary component of the microdroplet, but can be mixed with another compound which is liquid at 37° C. to adjust the overall HSP parameters of the solution.

Geraniol is a monoterpanoid alcohol which is the primary part of rose oil. It is used as a fragrance or flavouring agent. The HSP parameters for geraniol are $\delta_d$=16 $\delta_p$=4.7 $\delta_h$=11 $MPa^{1/2}$ and it's RED with cholesterol is 0.73 making it a good solvent for atherosclerotic plaque.

Nerol is also a monoterpene alcohol with a rose like odour found in the essential oils of lemon grass and hops. The HSP parameters for nerol are $\delta_d$=16.7 $\delta_p$=4.5 $\delta_h$=11.3 $MPa^{1/2}$ and the RED with cholesterol is only 0.62 making it a good solvent for atherosclerotic plaque.

Citronellol is a monoterpenoid found in rose oil and pelargonium germaniums. The HSP parameters for citronellol are $\delta_d$=16 $\delta_p$=4.7 $\delta_h$=10.7 $MPa^{1/2}$ and it's RED value with cholesterol is 0.72 making it a good solvent of atherosclerotic plaque.

Artemisia Ketone is a naturally occurring ketone used in fragrances and as a flavouring agent with a honey berry scent. The HSP parameters are $\delta_d$=15.9 $\delta_p$=5.8 $\delta_h$=5.1 $MPa^{1/2}$ and it's RED value with cholesterol is 0.83.

Citral is the primary component of the oil from the lemon myrtil plant and an aldehyde, with HSP parameters $\delta_d$=16.3 $\delta_p$=2.3 $\delta_h$=6.2 $MPa^{1/2}$. The RED value with cholesterol is 0.7.

Citronellal is a naturally occurring monoterpenoid with a lemon scent. The HSP parameters of citronellal are $\delta_d$=16.2 $\delta_p$=5.9 $\delta_h$=5.2 $MPa^{1/2}$ and it has an RED value with cholesterol of 0.78.

Linalyl Acetate is the acetate ester of linalool. Linalyl acetate is a naturally occurring compound which gives lavender its characteristic scent, with the HSP parameters of $\delta 6_d$=16 $\delta_p$=2.8 $\delta_h$=5.5 $MPa^{1/2}$. Linalyl acetate has a Relative Energy difference of RED=0.76 with cholesterol. The melting point is 85° C. and since it will be solid at core body temperatures, it could be used as an additive, but not the primary component of the biocompatible microdroplet.

Dipentene is a mixture of the two isolmers of limonene (racemic limonene), with $\delta_d$=16.7 $\delta_p$=2.2 $\delta_h$=4 $MPa^{1/2}$ and an RED=0.73 with cholesterol.

Terpinolene is a naturally occurring isomer (δ-terpenene) of terpenene, with HSP parameters of $\delta_d$=16.9 $\delta_p$=1.8 $\delta_h$=4.1 $MPa^{1/2}$ and a RED=0.70 with cholesterol.

Phellandrene are naturally occurring cyclic monoterpenes with HSP parameters of $\delta_d$=16.5 $\delta_p$=1.6 $\delta_h$=3.9 $MPa^{1/2}$ and RED=0.76 with cholesterol.

Sylvestrene is a mixture of two isomeric terpenes with HSP parameters of $\delta_d$=16.6 $\delta_p$=3 $\delta_h$=4.1 $MPa^{1/2}$ and a RED with cholesterol of 0.74.

Perillaldehyde is a naturally occurring monoterpenoid containing an aldehyde functional group, which is used as a food additive. The HSP parameters of perillaldehyde are $\delta 6_d$=17.1 $\delta_p$=6.9 $\delta_h$=5.9 $MPa^{1/2}$ and it has a RED of 0.68 with Cholesterol.

Pulegone is a naturally occurring organic compound classified as a monoterpene keytone. Pulegone has the HSP parameters $\delta_d$=17.5 $\delta_p$=8.9 $\delta_h$=5.5 $MPa^{1/2}$ and has a RED with cholesterol of 0.74.

Piperitone is a naturally occurring monoterpene ketone with the HSP parameters $\delta_d$=17 $\delta_p$=6.2 $\delta_h$=4.5 $MPa^{1/2}$ and RED with cholesterol of 0.72.

Menthone is a naturally occurring monoterpene and a keytone with the HSP parameters equal to $\delta_d$=17 $\delta_p$=8.1 $\delta_h$=4.4 $MPa^{1/2}$ and a RED=0.79.

1,4-Cineole is a naturally occurring monoterpene which exists in cubeb and chamomile. The HSP parameters of 1,4-cineole are $\delta_d$=17.1 $\delta_p$=3.6 $\delta_h$=3.7 $MPa^{1/2}$ and it's RED with cholesterol is 0.70.

Farnesol is a naturally occurring acyclic sesquiterpene alcohol with the HSP parameters of $\delta_d$=16.4 $\delta_p$=3.8 $\delta_h$=7.7 $MPa^{1/2}$ and RED with cholesterol of 0.65.

Squalene is a naturally occurring hydrocarbon, with 30 carbon atoms, and is classified as a triterpene molecule. It is produced natuarally by the organism, and is found in abundance in shark liver oil. Despite its larger molecular size, it is liquid at 5° C. The HSP parameters for squalene are of $\delta 6_d$=17.6 $\delta_p$=3 $\delta_h$=6 $MPa^{1/2}$ and a RED with cholesterol of 0.52.

- Nerolidol is a naturally occurring sesquiterpene found in ginger. Nerolidol has HSP parameters of $\delta_d$=16.4 $\delta_p$=2.7 $\delta_h$=8.7 MPa$^{1/2}$ and a RED with cholesterol of 0.64.
- Bisabolene is a naturally occurring sesquiterpene which is found in cubeb, lemon and oregano. Bisabolene has the HSP parameters of $\delta_d$=16.7 $\delta_p$=2.2 $\delta_h$=4 MPa$^{1/2}$ and a RED=0.73 with cholesterol.
- Zingiberene is a monocyclic sesquiterpene which is a major component of ginger oil, and gives ginger its characteristic flavour. Zingiberene has the HSP parameters of δ6$_d$=16.6 $\delta_p$=1.4 $\delta_h$=4.1 MPa$^{1/2}$ and a RED=0.74 with cholesterol.
- Diethyl carbonate (CAS:105-58-8) is an organic compound with extremely low toxicity, with a reported LD50 of 8.5 g/kg (oral). The HSP parameters for diethyl carbonate are $\delta_d$=16.6 $\delta_p$=3.1 $\delta_h$=6.1 MPa$^{1/2}$ and the RED with cholesterol is 0.65 which also make it a good solvent for atherosclerotic plaque.
- Benzyl benzoate is an organic compound with very low toxicity, which is rapidly hydrolized to benzoic acid and then eliminated in urine. It is insoluble in the water based blood with HSP parameters of $\delta_d$=20 $\delta_p$=5.1 $\delta_h$=5.2 MPa$^{1/2}$ and a very low RED=0.39 making it a very good solvent of cholesterol in atherosclerotic plaque. The LD50 dose for benzyl benzoate is 1.68 g/kg. Note worthy is the large dispersion coefficient of this molecule, which is the primary reason why it has such a low relative energy difference with cholesterol.
- Diphenyl ether is an organic compound used in soaps and some fragrances. It is also used in manufacturing and hence there is considerable data on its toxic effects. The LD50 dose for diphenyl ether is 2.85 g/kg of body weight and there are no long term health effects. The HSP parameters are $\delta_d$=19.5 $\delta_p$=3.4 $\delta_h$=5.8 MPa$^{1/2}$ and it has a RED=0.32 with cholesterol making it a very good solvent for cholesterol All of the substances listed in the preceding paragraphs occur naturally in foods and can be absorbed and metabolized by a patient. As with fatty acids, given they are water insoluble, they must be transported through the cardiovascular system on blood proteins or lipoproteins, and as such, will never form discrete droplets within the cardiovascular system, or make contact with atherosclerotic plaque. All these substances have Hansen Solubility Parameters which provide a relatively low relative energy difference (RED) with cholesterol, which makes them good solvents of atherosclerotic plaque. Many of these chemicals have very low toxicity, and are metabolized via different pathways, which can be leveraged to create a multi-component biocompatible solvent with low toxicity.

BRIEF DESCRIPTION OF DRAWINGS

FIG. 1: Illustration showing the mechanism by which the plaque is dissolved by the microdroplets of the biocompatible microdroplet solvent emulsion means travelling through an artery.

FIG. 2: Diagram showing the surface energy density at the microdroplet/blood interface and microdroplet/cholesterol interface.

FIG. 3: Chart showing the reduction in surface energy as a microdroplet attaches to a surface comprised of cholesterol vs. position.

FIG. 4: Chart showing the attractive force between the microdroplet and cholesterol surface vs. position.

FIG. 5: Portable emulsifier to emulsify the biocompatible microdroplet solvent prior to administration.

FIG. 6: Diagram showing the procedure used to formulate the biocompatible microdroplet solvent emulsion means.

FIG. 7: Diagram showing the procedure to formulate a biocompatible microdroplet solvent emulsion means with three components, to arrive at a small RED value with cholesterol.

FIG. 8: Apparatus for the controlled administration of the biocompatible microdroplet solvent emulsion means, with inline emulsifier, and optional filtration system.

FIG. 9: Catheter tip with miniature perforations suitable for the generation of microdroplets directly within a blood vessel.

FIG. 10: Catheter with specially designed tip to generate the microdroplets directly in a patients blood vessel. Using this specially designed catheter, the biocompatible solvent (as opposed to an emulsion) can be used and injected directly into a blood vessel.

FIG. 11: Hansen Solubility Parameters of cholesterol, water, select alcohols, and fatty acids, along with their Relative Energy Difference (RED) with cholesterol, summarized as Table 1.

FIG. 12: Hansen Solubility Parameters (HSP) of select monoterpene and sesquiterpene compounds along with their Relative Energy Difference (RED) with cholesterol, summarized as Table 2.

FIG. 13: Hansen Solubility Parameters of select monoterpene keytones as well as some monoterpenoids along with their Relative Energy Difference with cholesterol, summarized as Table 3.

FIG. 14: Hansen Solubility Parameters of select monoterpene and sesquinterpene alcohols, as well as diverse compounds, summarized as Table 4.

DETAILED DESCRIPTION OF PREFERRED EMBODIMENT

FIG. 1 is a pictorial highlighting the underlying principle of the invention. The water insoluble biocompatible solvent microdroplet means 102 are injected into the blood stream by injection means 106 and travel through a patient's arteries 101. In this figure, injection means 106 is placed in an artery, slightly upstream of the arterial plaque being treated. However, given that the microdroplets are small enough to pass unobstructed through capillaries, the injection means 106 could comprise of a simple needle to inject the biocompatible microdroplet solvent emulsion in any perfuse tissue or vein, or could be a venous catheter or an arterial catheter as shown in FIG. 1 or any other device used to inject a fluid intravenously.

Once the microdroplets of biocompatible solvent enter the cardiovascular system, they will gradually be drawn towards the arterial system, where they will make contact with arterial plaque 103. When they make contact with arterial plaque 103, the microdroplets 102 will bind to the arterial plaque 103 and small amounts of cholesterol, cholesterol esters or other fatty compounds in the arterial plaque will dissolve into the microdroplet 104. When sufficient quantity of microdroplets have accumulated on the plaque, some microdroplet solvent 105 which now contains dissolved cholesterol, cholesterol esters or other elements of the plaque will be washed downstream by the flowing blood and carry the dissolved cholesterol or plaque through the blood stream until it is eventually solubilised and metabolized along with the cholesterol it carries.

Over several hours, billions of microdroplets of the biocompatible solvent will travel through a patient's cardiovascular system and safely reduce the quantities of arterial plaque in a patient's cardiovascular system. By way of example, if 2 $cm^3$ of biocompatible solvent are emulsified with saline, and the average radius of a microdroplet is 500 nm, there would be approximately 3.8 trillion microdroplets. Furthermore, the total external surface area of the microdroplets would amount to approximately 12 square meters, sufficient to coat the interior lumen of most diseased arteries several times over. The extremely large number of microdroplets, combined with a large aggregate surface area of the microdroplets, and the fact that they will selectively bind to free cholesterol or cholesterol esters in arterial plaque due to energy principals, provides a very selective and effective treatment option for atherosclerosis.

This system offers a systemic method of treating the build up of plaque in all blood vessels, safely and with minimal side effects. Alternatively by the use of a catheter placed directly in an artery with a known blockage or build up of plaque, a very focused treatment to a diseased artery can be achieved as well as all downstream branches and provide an alternative to angioplasty. One of the primary benefits of this method compared to angioplasty is that the plaque is actually removed and there is no damage to the blood vessel since the artery does not need to be stretched and held open with a stent. Furthermore, in addition to treating a single narrowed section of an artery, the microdroplets of the biocompatible solvent will treat all accumulations of plaque which are downstream from the catheter which is injecting the microdroplets of biocompatible solvent on a first pass through the cardiovascular system, and could be used to treat small vessel disease. Microdroplets which did not attach to arterial plaque on the first pass through the arterial system, will be recirculated from the venous to the arterial system and will benefit all arteries. Manifestation of atherosclerosis in small vessels of the brain are often referred to as cerebral small vessel disease, small vessel ischemic disease, white matter disease, periventricular white matter changes, perivascular chronic ischemic white matter disease of aging, white matter hyperintensities, age-related white matter changes and leukoaraiosis. In addition, similar conditions can affect the heart. When the small arteries of the heart are impaired due to atherosclerosis, this condition is known as coronary microvascular disease (MVD).

If the biocompatible microdroplet solvent means is injected in a vein, or perfuse tissue, the microdroplets will gradually make their way through the venous system to the heart, where they will be circulated through all arteries, thereby providing a systematic treatment benefiting all arteries. In principal, the microdroplets will not all bind to atherosclerotic plaque on the first pass through the artery, and will be recirculated multiple times.

An ability to treat smaller arteries of the heart or brain or other major organs, is a major advantage of this technology. Research has shown that many disorders of the brain, such as dementia, Parkinson's disease and even Alzheimer's are very strongly correlated to the narrowing of arteries in the brain. Autopsies on elderly citizens has shown many actually had small strokes, in some cases many small stokes, which had never been reported, diagnosed or treated. These small strokes result in voids within the brain and are believed to be a contributing factor to cognitive decline, memory loss and eventually dementia. Similarly, atherosclerosis in the small arteries of the heart is called Coronary Microvascular Disease (MVD). There are relatively few treatment options for atherosclerosis in smaller arteries. This new technology will provide a direct method to treat small arteries given the microdroplets will travel through all arteries, with the number of droplets passing through a given artery approximately proportional to the blood flow through the said artery. Finally, it is important to mention that the microdroplets of biocompatible solvent will continue to dissolve arterial plaque until they are metabolized, or bound to blood proteins. They will circulate from the venous system, to the arterial system and back many times prior to being solubilised and will have many opportunities to come into contact and bind to free cholesterol, cholesterol esters or fatty materials within the plaque.

The biocompatible solvent microdroplet means should be sufficiently insoluble in water and blood to allow the microdroplets to travel from the injection point, to the arterial plaque, without having a significant portion of the microdroplet be dissolved in the blood. Furthermore, the microdroplet should have solubility parameters which are well matched to those of cholesterol, cholesterol esters or other fatty material of components of the plaque we are trying to remove. To ensure selectivity to arterial plaque, the surface energy density between the microdroplet and the free cholesterol in arterial plaque should be very low compared to the surface energy at either of the cholesterol/blood interface or the microdroplet/blood interface. Having a relatively low surface energy at the microdroplet/cholesterol interface ensures the microdroplets will selectively bind to the cholesterol and ensure the microdroplet will wet the free cholesterol. Finally, the microdroplets should be reasonably non-toxic in the quantities one will need to administer. If the injection is administered in a vein or any perfuse tissue, small doses can be administered on a daily or weekly basis. The dose of biocompatible solvent microplet means could be as small as a few cubic millilitres, to a couple hundred millilitres, depending on toxicity of the compound used to produce the microdroplets. If the biocompatible microdroplets are emulsified with saline to form an emulsion, the quanity of the biocompatible microdroplet solvent emulsion means could be even larger, potentially as much as 1 litres per dose. The biocompatible solvent would need to be emulsified with a hydrophilic or water based carrier. The most likely carrier would be saline given that it can be administered intravenously with no adverse side effect. The emulsification process should be mechanical in nature, such as high energy ultrasonic emulsification, given that a chemical emulsifying agent such as a surfactant is undesirable since it would reduce the surface energy density at the droplet/blood interface, and make them less selective to cholesterol. Alternatively, the author has devised of a novel catheter with a micromachined tip which can be used to generate the microdroplets directly in a patients blood vessel, as the biocompatible solvent means is being pushed through the catheter. Use of this specialized catheter which will be described in detail later, eliminates the need to emulsify the solvent with a saline carrier prior to administration.

Surface Energy as a Means of Ensuring Selectivity

Given that a relatively small quantity of the biocompatible microdroplet solvent emulsion will be used with each dose, combined with the comparatively large blood volume and a large internal luminal surface area of the cardiovascular system, it is desirable that the microdroplets selectively bind to arterial plaque, as opposed to other surfaces within the cardiovascular system.

One of the several innovative aspects of the present invention is that the microdroplets are being designed to have similar HSP parameters to the cholesterol in arterial plaque, and will therefore have a very low surface energy density at the microdroplet/cholesterol interface. Comparatively, the surface energy density between the microdroplet and the blood plasma or the microdroplet and the phospholipid bilayer of blood cells or the endothelial cells which line the walls of healthy arteries, veins and capillaries, will be much higher. The microdroplets will naturally seek to occupy the lowest energy state, and will preferentially bind to the cholesterol, cholesterol esters or other hydrophobic compounds in the arterial plaque. The fact that the microdroplet binding to the free lipids in arterial plaque represents a low energy state, provides a physical mechanism which will tend to enhance the selectivity of microdroplets to arterial plaque. Upon making contact with cholesterol in arterial plaque, surface tension will hold the microdroplet to the plaque, and will cause it to spread and cover the plaque, thereby dissolving cholesterol. Other surfaces within the cardiovascular system are hydrophilic, and will have solubility parameters which are well match to those of the water based blood plasma. As such, the microdroplet of biocompatible solvent will be repelled from these other surfaces, and will continue to circulate within the cardiovascular system. For example, the outer surface of the cell membrane is covered by polar heads of phospholipids which allows them to be immersed in the water based blood plasma without experiencing a large surface tension at the blood/membrane interface. The microdroplets of the biocompatible solvent means will be repelled by these other surfaces, and as such will selectively bind to the cholesterol, cholesterol esters or other compounds within the plaque with which they have a low interfacial surface energy density.

FIG. 2 shows the surface energy density at different interfaces in a microdroplet 110/cholesterol 115 system. Initially, a spherical microdroplet 110 travels through the blood stream. The surface energy between the blood and the microdroplet is approximately 0.05 $J/m^2$. This is shown as the Blood/Microdroplet Surface Energy Density 112 in the figure. This value of surface energy density is typical for a hydrophobic oil based droplet in whole blood. For pure water the surface energy density would actually be approximately 0.07 $J/m^2$. Similarly, the free cholesterol in the arterial plaque is a hydrophobic surface and the blood/cholesterol interface 113 also has a surface energy density of approximately 0.05 $J/m^2$. The interface between the microdroplet and the free cholesterol 114 in the arterial plaque is an area of low surface energy density, given that both substances are hydrophobic, and the microdroplet was constructed from a compound or mixture of compounds which have similar solubility parameters to cholesterol. As such the surface energy density between the cholesterol and microdroplet is much lower than between the microdroplet and blood, or cholesterol and blood.

As the microdroplet spreads 111 over the cholesterol surface 114, there will be a sharp reduction in energy of the cholesterol/microdroplet system. This change in energy will result in a binding force between the microdroplet and the cholesterol surface. For small microdroplets, the actual force expressed as a force per unit area or pressure, is surprisingly large, and is far greater than the shear stresses exerted on the microdroplet by the flowing blood at the artery wall.

For the sake of highlighting the operating principal, and providing a quantitative measure to the attractive force and binding pressure between the microdroplet and the free cholesterol, cholesterol esters or fatty compounds in the atherosclerotic plaque, the author has derived the equations below and provides them as reference. However, these equations have not been verified by a third party and any error or omission should not be used to detract from the inventive spirit of the invention disclosed herein. They are purely provided by way of example to explain the operating principal in greater detail.

From mechanics and basic principles the change of energy of the microdroplet/cholesterol system can be expressed as:

$$\Delta E = \text{Work} = \text{Force} \cdot \text{distance} \qquad \text{Eq. 3}$$

Change of energy arises from a change in the surface energy as the droplet changes from a spherical microdroplet 110 fully surrounded by water based blood, with a large surface energy density on all its surface, and begins to compress against the water insoluble cholesterol 115 on the artery wall where the surface energy density at the microdroplet/cholesterol interface 114 is substantially lower than at the blood/microdroplet interface. The Force is created by the difference in surface tension on the microdroplet/blood surface 112 vs. the microdroplet/cholesterol surface 114. Note that surface tension and surface energy density discussed within the context of FIG. 2 are actually the same thing, and have the same magnitude, although when referring to surface tension the units of N/m are used, while for Surface Energy Density, the units of $J/m^2$ are used ($N/m*m/m=J/m^2$).

Surface energy of the microdroplet/cholesterol system can be expressed as:

$$E = \gamma_{b\text{-}ch} A_{b\text{-}ch} + \gamma_{b\text{-}md} A_{b\text{-}md} + \gamma_{ch\text{-}md} A_{ch\text{-}md} \qquad \text{Eq. 4}$$

Where $\gamma_{b\text{-}ch}$, $\gamma_{b\text{-}md}$, $\gamma_{ch\text{-}md}$ are the surface energy density of the blood-cholesterol, blood-microdroplet and cholesterol-microdroplet interfaces respectively, and $A_{b\text{-}ch}$, $A_{b\text{-}md}$ and $A_{ch\text{-}md}$ are the surface area of the free cholesterol/blood interface, the blood/microdroplet interface and cholesterol/microdroplet interface respectively.

The above equation can be simplified by assuming that the surface energy density at the blood/cholesterol interface is approximately the same as the blood/microdroplet interface, and by further assuming that the surface energy density at the cholesterol/microdroplet interface is approximately 0. In practice they do not need to be exactly the same, but it is only necessary that the microdroplet/cholesterol interface have significantly lower surface energy density than either the cholesterol/blood or microdroplet/blood interfaces. If we then look purely at the surface energy which is affected by the presence of the microdroplet, we obtain:

$$E = \gamma (A_{b\text{-}md} - A_{ch\text{-}md}) \qquad \text{Eq. 5}$$

Where $\gamma$ is the surface tension or surface energy in $J/m^2$ at the blood/cholesterol and blood/microdroplet interface which are assumed to be approximately of equal magnitude and $A_{b\text{-}md}$ is the area of the microdroplet facing blood and therefore having a high surface energy, while $A_{ch\text{-}md}$ is the area of the cholesterol which is now covered by the droplet. The cholesterol/blood interface is assumed to have a high surface energy given cholesterol is insoluble in blood, while the microdroplet/cholesterol interface is assumed to have very low surface energy given the microdroplet's solubility properties are designed to be very close to those of cholesterol.

Assuming the microdroplet takes the shape of a progressively flatter spherical cap as it compresses against the cholesterol, and recalling that for a spherical cap, the top curved surface facing the blood would have an area of:

$$A_{b\text{-}md} = 2\pi h \qquad \text{Eq. 6}$$

And the flat surface facing the cholesterol would have an area of:

$$A_{ch\text{-}md}=\pi a^2=\pi h(2r-h) \quad \text{Eq. 7}$$

Substituting Eq. 6 and Eq. 7 back into Eq. 5 we obtain:

$$E=\gamma\pi(2rh-2rh-h^2)=\gamma\pi h^2 \quad \text{Eq. 8}$$

In the above equation, r is the radius of the microdroplet spherical cap, and h is the distance from the top of the spherical cap, to the surface of the cholesterol to which it is attaching. Differentiating E with respect to h, we obtain the force with which the microdroplet is being pushed against the cholesterol:

$$F=\frac{dE}{dh}=2\gamma\pi h \quad \text{Eq. 9}$$

Referring now to FIG. 4, we have a curve for the binding force versus $h/D_o$ for two different microdroplet radiuses. The first curve 133 shows the force vs. $h/D_o$ for a microdroplet with an initial radius of 1 micron, whereas curve 134 shows the force versus $h/D_o$ for a microdroplet with an initial radius of 500 nm. The force is actually proportional to the radius of the microdroplet, given that h is actually equal to 2r, just prior to having the microdroplet 130 touch down on the cholesterol. Immediately upon contact 135, the force is the strongest and decreases gradually as the microdroplet spreads over the cholesterol surface to assume the shape of a progressively flatter spherical cap 131 and then 132.

Referring next to FIG. 3, which once again shows the surface energy vs. h/Do for a microdroplet with a 1 micron radius 123 and a 500 nm radius 124. Immediately upon contact 120, there is a reduction in energy of the system as the microdroplet covers an area $A_{ch\text{-}md}$, on the surface of the cholesterol, which was previously in contact with blood. This sudden decrease in energy results in a binding force between the microdroplet and the cholesterol. For a typical microdroplet radius of 1 micrometer, the binding force at contact, is on the order of 900 nN. The binding force decrease as the microdroplet flattens against the cholesterol and assumes the shape of a progressively flatter spherical cap 121 and 122.

From FIG. 4, a force of 900 nanonewtons may seem like an extremely small force, but if we consider that this force is being applied to a droplet with a radius of 1 micrometer, we find that the force divided by the cross section is actually extremely high, 900 nN/$(\pi 10^{-6}$ m$)^2$=286 kPa. This binding pressure is very large and sufficient to cause the microdroplet of biocompatible solvent to remain attached to the cholesterol, despite the flowing arterial blood. The binding pressure will increase inversely with the diameter of the droplet, and can become extremely large for very small droplets. For comparison, the total systolic blood pressure, between the arterial trunk and veins is on the order of 18 kPa. As such, the shear stress at the edges of the artery would be considerably less than 18 kPa, and insufficient to pull the microdroplet away from the cholesterol. Gradually, as a multitude of microdroplets accumulate on an area of arterial plaque, and a thin film of biocompatible solvent begins to develop, the binding pressure will be reduced due to the large surface area, and some solvent will shear off and droplets will be pulled downstream, away from the plaque. Gradually, the solvent of the biocompatible microdroplet, and dissolved cholesterol, will be broken down and metabolized by the patient.

Given that any physical system will gradually seek to occupy the lowest energy state, we have thus shown from energy principles that a biocompatible microdroplet emulsion can be made to selectively bind to free cholesterol or cholesterol esters in arterial plaque as opposed to other hydrophilic surfaces in the cardiovascular system. The microdroplets will continue to circulate in the cardiovascular system until such time as they make contact with free cholesterol in arterial plaque, and will attach themselves to the free cholesterol upon making contact.

However, to achieve this large selectivity, it is important that the microdroplets have a high surface energy density at the microdroplet/blood interface, and a comparatively low surface energy density at the microdroplet/cholesterol interface. This requirement would imply that the microdroplets also have a high surface energy density at the microdroplet/saline interface, and the solution would have a poor thermodynamic stability, and a relatively short shelf life, given that the microdroplets would tend to coalesce. This requirement is in contrast to microemulsions which are used in the biomedical, pharmaceutical or food processing industries where a thermodynamically stable emulsion is desired to achieve a long shelf life. As discussed previously, to achieve this thermodynamic stability, a chemical emulsifier or surfactant is added to the oil based compound, and mixed into the droplets during the emulsification process.

For the purposes of the current invention use of a surfactant would decrease or even eliminate the selectivity of the microdroplets to cholesterol, We desire a microdroplet emulsion which is less thermodynamically unstable. A primary objective of the biocompatible microdroplet solvent emulsion means is that the microdroplets bind and attach to free cholesterol or cholesterol esters in atherosclerotic plaque on contact. The ideal outcome is that within several minutes of being injected into the cardiovascular system, most microdroplets will have come into contact with the free cholesterol or cholesterol esters in arterial plaque, and will have attached themselves to the cholesterol. To achieve this, it is necessary that the microdroplets have a very low surface energy density at the cholesterol/microdroplet interface, compared to the blood/microdroplet interface. The use of a surfactant to reduce the surface energy density at the microdroplet/water interface would tend to make the droplets more thermodynamically stable within the water based blood, and eliminate the tendency of these microdroplets to attach to and dissolve the cholesterol in arterial plaque. This is a very key and fundamental difference between the biocompatible microdroplet emulsion of this invention, and microdroplet emulsions being produced for other applications.

Referring now to FIG. 6, this diagram provides a flow chart showing how the biocompatible microdroplet solvent emulsion can be formulated. The first step is to select compounds from the set of known compounds 400, which have acceptably low toxicity when administered intravenously, and have Hansen Solubility Parameters which are suitable for dissolving cholesterol. For an example of compounds which might be included in 400, please refer to Tables 1, 2, 3 and 4. However, this list of tables is by no means exhaustive and other compounds could be added to this list. The number of compounds selected can comprise of 1, 2, 3 or as many as are deemed necessary, which is symbolized by the variable n. The HSP parameters of a homogenous mixture of compounds are the weighted average of the HSP parameters of the individual components. As such, the compounds can be selected with a desired volumetric fraction $f_1, f_2, f_3, \ldots f_{n-1}, f_n$, where n is the number of compounds used, such that the resultant HSP parameters are a good match to those of cholesterol and or other components of arterial plaque. Ideally, it is possible to formulate a solution such that the resultant RED of the mixture is smaller than the RED of any of the individual components. As shown in process box 401, this objective can be expressed mathematically as:

$$\delta_{hm} = \sum_{i=1}^{n} f_i \delta_{hi} \quad \delta_{pm} = \sum_{i=1}^{n} f_i \delta_{pi} \quad \delta_{dm} = \sum_{i=1}^{n} f_i \delta_{di} \qquad \text{Eq. 9}$$

$$RED_{mixture} = \frac{\sqrt{4(\delta_{dm} - \delta_{dc})^2 + (\delta_{pm} - \delta_{pc})^2 + (\delta_{hm} - \delta_{hc})^2}}{R_o} \qquad \text{Eq. 10}$$

The $\delta_{dm}$, $\delta_{pm}$, $\delta_{hm}$ calculated using Eq. 9 are the Hansen solubility parameters of the homogenous mixture, where m denotes mixture, and $f_i$ depicts the fraction of each of the n components used to fabricate the biocompatible solvent. Equation 10 can be used to calculate the RED of the final mixture, where Ro is the interaction radius of the cholesterol, or other component of arterial plaque one desires to dissolve using the biocompatible microdroplets and $\delta_{dm}$, $\delta_{pm}$, $\delta_{hm}$ represents the Hansen solubility constants of cholesterol (dispersion, polar and hydrogen bonding components) or the HSP parameter of the arterial plaque which is being targeted.

As mentioned previously, a second benefit to using multiple components in the biocompatible solvent is to reduce toxic side effects. By choosing compounds which are metabolized or eliminated differently, any side effects can be greatly reduced, and a larger quantity of biocompatible solvent can be administered with each treatment. Using a larger quantity of biocompatible solvent will allow the treatment to dissolve additional cholesterol, and increase the efficacy of the treatment protocol.

Once the solvent is ready, all components of the biocompatible solvent produced in 401 can be combined with saline 402 and mixed in step 403. If the solvent will be used imminently, it can be mixed using a high energy mechanical agitation in step 403 and then broken down into a microemulsion using high power ultrasonic emulsification in 404. Ultrasonic emulsification is known to be able to break microdroplets down to an average diameter which is less than 1 micron, and to offer excellent control on the dispersion of droplet diameters. Alternatively, if the product will not be used for several weeks, the saline/biocompatible solvent can be sealed in step 403, and the final mixing and ultrasonic emulsification of step 404 can be performed at the point of care, prior to injecting the biocompatible microdroplet solvent emulsion means into the patient.

Referring now to FIG. 7, a specific composition of a biocompatible microdroplet solvent microemulsion is provided which yields a very low RED. This composition comprises of three compounds which have been included in 500, specifically benzyl benzoate, diphenyl ether and eugenol. Benzyl benzoate has the dispersion coefficient which is closest to cholesterol, while diphenyl ether has the polar coefficient which is closest to cholesterol and eugenol has a hydrogen bonding parameter which is slightly larger than cholesterol. By using space mapping methods or other analytical or numerical methods, the fraction of each component can be changed to evaluate the overall response of the Relative Energy Difference to the change of fractional content of a given compound. In this way, the fraction of each component can be found which will give the smallest RED value. In the example above, the optimal fraction is 25% benzyl benzoate, 45% diphenyl ether and 30% eugenol as shown in 511, 512 and 513. Calculating the resultant HSP parameters for the solution as well as the RED in 501, the values are found to be $\delta_{dm}$=19.2, $\delta_{pm}$=4.94, $\delta_{hm}$=7.4 The resultant RED is 0.30, which is smaller than any of the RED of the individual components. Other analytical or numerical methods could be used to find the optimal ratio of each compound. For the sake of clarity the individual HSP parameters and fractional content of each compound is provided in table 5 below.

TABLE 5

Example where multiple compounds are mixed to give a mixture with HSP parameters which are a better match to those of cholesterol.

| Component | Chemical | CAS # | | HSP Parameters ($MPa^{1/2}$) $\delta_d$ | $\delta_p$ | $\delta_h$ | Ro | $Ra^2$ | RED |
|---|---|---|---|---|---|---|---|---|---|
| Plaque | Cholesterol | | $C_{27}H_{46}O$ | 20.4 | 2.8 | 9.4 | 12.6 | | |
| A | benzyl benzoate | 120-5-4 | $C_{14}H_{12}O_2$ | 20 | 5.1 | 5.2 | | 24 | 0.39 |
| B | diphenyl ether | 101-84-8 | $C_{12}H_{10}O$ | 19.5 | 3.4 | 5.8 | | 17 | 0.32 |
| C | Eugenol | 97-53-0 | $C_{10}H_{12}O_2$ | 18.1 | 7.1 | 11.6 | | 44 | 0.53 |

| Fraction of Each Component in mixture A | B | C | | HSP Parameters ($MPa^{1/2}$) $\delta_d$ | $\delta_p$ | $\delta_h$ | $Ra^2$ | RED |
|---|---|---|---|---|---|---|---|---|
| 25% | 45% | 30% | Mixture | 19.205 | 4.935 | 7.39 | 14 | 0.300 |

A secondary but very important benefit of using multiple compounds, is that the undesireable toxic side effects can be reduced compared to the use of a single component, since each chemical is metabolized differently. For example, benzyl benzoate once absorbed, is broken down to benzoic acid, with benzyl alcohol being a possible intermediary. Benzoic acid is excreted in the urine within 24 hours of ingestion. Eugenol forms conjugates with sulphate, the major metabolites are glucuronic acid conjugate. Diphenyl ether once absorbed, is primarily excreted in the urine (90%) while a small percentage is broken down into its 2-hydroxy, 4-hydroxy, 4,4'-dihydroxy, 4-methoxy-monohydroxy and 4-methoxy-dihydroxy derivatives. Multiple compounds could be used as part of the biocompatible microdroplet solvent, each with different metabolic pathways to reduce the overall toxicity of the treatment. For example, if a large number of compounds are used, and they are carefully chosen to have different metabolic by products, a solvent with very low toxicity could be produced, which would allow a larger quantity of biocompatible microdroplet solvent emulsion means to be used.

The biocompatible microdroplet solvent emulsion means could be fabricated from a multitude of compounds without departing from the spirit of the invention. Some formulations could be contrived which have very low toxicity, but a relatively poor RED value with arterial plaque in the range of 0.8 or even 0.9, but given that a larger quantity of biocompatible solvent can be used, the overall efficacy is significant. Other compositions may strive for a very good solubility match to cholesterol, with a RED<0.5 or even 0.4 or <0.3 as shown in table 5, and have a slightly higher toxicity but given that the solubility match is better, may achieve a comparable efficacy with a smaller quantity of biocompatible microdroplet solvent emulsion means. Also, there are different types of plaque. It is conceivable that different formulations of the biocompatible microdroplet solvent emulsion means will offer the best efficacy on different type of plaque. Plaque in arteries of the brain which is linked with a high incidence of Alzheimers may have a different composition than arterial plaque in the coronary arteries. Plaque in small arteries could respond different than plaque in larger arteries. Plaque in arteries where blood velocity is high due to a narrowed cross section, may respond better to certain types of biocompatible microdroplets solvent emulsion means, than plaque in arteries where the blood velocity is slower. Old plaque which is calcified may respond differently than newer plaque and may require a different formulation. Many future formulations may be developed without departing from the spirit of the invention. It is conceivable that treatments could be developed that use two or more different types of biocompatible microdroplet solvent emulsions, administered simultaneously, or staggered in time. The primary degrees of freedom when deriving new biocompatible microdroplet solvent emulsion means will be the compounds used to create the solvent, the size of the microdroplets, the resultant HSP parameters and the RED value with the type of plaque being treated, as well as the surface energy density between the microdroplet and the plaque, or the microdroplet and other components of the cardiovascular system, and finally the type of metabolizes which are created as the patient metabolizes and eliminates the biocompatible microdroplet solvent emulsion means post administration. For a given formulation, the mean microdroplet diameter may also be an important degree of freedom, since the binding pressure is inversely proportional to droplet diameter, and smaller microdroplets may diffuse through the plaque more effectively. All these degrees of freedom may be adjusted as new formulations are tested and optimized for a specific manifestation of atherosclerotic disease, without departing from the spirit of the invention.

The ideal biocompatible solvent should have Hansen Solubility Parameters which are well matched to cholesterol, cholesterol esters or other components of the arterial plaque we desire to treat to allow a sufficiently large quantity of plaque to be dissolve for a given quantity of biocompatible solvent, and have a calculated Relative Energy Difference (RED value) of less than 1.0, but preferably less than 0.8 and ideally less than 0.7 or even 0.6. Tables 1-4 shows a few of the compounds which have been shown experimentally to be effective at dissolving cholesterol. Fatty acids with a RED with cholesterol of less than 0.8 are quite common as can be seen in Table 1. Typically, a solution with an RED of approximately 0.8 will dissolve a mass fraction of approximately 8% cholesterol. Most mono or polyunsaturated fatty acids are insoluble in water and have an RED with cholesterol of ~0.8. Many of the terpenoids, terpenes and their derivatives have reasonably low toxicity and given many have a cyclic structure, tend to have a higher dispersion coefficient despite a lower carbon count. As such, they tend to be good solvents of cholesterol and can have a RED which is less than 0.7, but many have RED values which are lower than 0.6. All of the chemicals listed in Tables 2-4 have RED values which are less than 0.8 with the exception of Artemisia ketone. Several compounds from the terpenoid family have RED values with cholesterol which are less than 0.7, specifically limonene, terpenene, ocimene, acetophenone, menthol, nerol, farnesol, nerolidol, carvacrol and perillaldehyde. A few terpenoids have RED values which are less than 0.6, specifically carvone, terpeneol and eugenol. Finally, a few organic compounds with low toxicity and small RED value were identified, specifically diethyl carbonate (RED=0.66), benzyl benzoate (RED=0.39) and diphenyl ether (RED=0.32). Ultimately, the preferred compound from which to fabricate the micrdroplets depends on the efficacy with which they bind and dissolve arterial plaque in-vivo, combined with undesireable side effects. A compound which is less effective, but which can be used in a larger quantity may be preferred to a compound with a better solubility match but which must be used in a smaller quantity. Mixtures of solvents can be used to arrive an RED values which are below 0.3. In the example provided in FIG. 7, a mixture of 25% benzyl benzoate, 45% diphenyl ether and 30% eugenol has an RED of 0.3 with cholesterol. A two part mixture of 60% benzyl benzoate and 40% diphenyl ether yields an RED=0.289. Although the RED is slightly lower than that of the three part mixture of table 5, it must be pointed out that this solution has a considerably larger fraction of benzyl benzoate, 60% vs. 25%. As such, if toxic effects induced by benzyl benzoate were the most toxic consequence of this particular set of biocompatible solvents, one would be able to use considerably more of the solution shown in table 5, that the two part mixture described in this paragraph.

The biocompatible microdroplet solvent emulsion means can be administered stand alone as a regular injection to perform a daily or weekly treatment. In this scenario, the injection could be directly in a vein or perfuse tissue such as a muscle. Once in the vein, the droplets of biocompatible solvent would be drawn towards the heart and pumped into the arterial system. Given that the microdroplets can be made to have a diameter which is inferior to 4 microns, they will pass unimpeded through the capillaries of the lung. Furthermore, a microdroplet has a relatively large internal pressure, as per the Young-Laplace equation, which greatly exceeds the pressure gradients within the heart and will therefore not be broken up by the pumping action of the heart. Once the microdroplets enter the arteries, they will bind to free cholesterol in arterial plaque upon making contact and dissolve cholesterol in the plaque. If the microdroplet does not make contact with arterial plaque on the first pass through the arterial system, it will continue to circulate until it makes contact with plaque or until it is eventually solubilised and dissolved by blood proteins.

The Young-Laplace equation can be used to calculate the internal pressure of a microdroplet as follows:

$$\Delta P = 2\gamma / r$$

Where:

γ is the surface tension at the microdroplet/blood interface, which will be approximately 0.05 N/m or 0.05 $J/m^2$ and r is the radius of the microdroplet. For a microdroplet with a diameter of 4 microns, the internal pressure is on the order of 50 kPa, which is nearly 3× larger than the systolic pressure of the cardiovascular system. The systolic pressure is the maximum pressure of the arterial system relative to atmospheric pressure, and is the total pressure between the arteries and veins. The pressure differential exerted on the microdroplet from flowing blood would be an extremely small fraction of this, and therefore the microdroplets will remain nearly spherical and travel through the cardiovascular system without being broken apart or deformed. For smaller radius diameters, for example 500 nm, the internal pressure increases to 200 kPa.

The small microdroplets would then be pushed into the arterial system where they would collide and come into contact with plaque in the various arteries, thereby attaching to and dissolving small quantities of plaque and helping to reduce or reverse atherosclerosis in the patient. This type of periodic treatment would be administered over an extended period lasting many weeks or even years to provide a systemic treatment and a gradual reduction in arterial plaque throughout the entire cardiovascular system If excessive amounts of the biocompatible microdroplet solvent are injected into the patient and the individual is feeling unwell, an injection of human albumin could be administered to bind with the fatty acid or lipids within the biocompatible microdroplets and allow it to be rapidly metabolized.

The quantity of microdroplets of biocompatible solvent which is injected and the rate at which it is injected are also important. On average, a human has about 5 litres of blood, of which 55% is blood plasma, and of this approximately 6-8% of it is blood proteins. A typical human will have approximately 165 to 220 ml of blood protein within their cardiovascular system. The albumin molecule is relatively large and has an approximate weight of 66000 atomic mass units (AMU) and although the volume of blood albumin is significant, there are only about 3 mmol of albumin molecules.

In a biocompatible microdroplet solvent means containing the equivalent of 2 g of biocompatible solvent, where the average molecular weight of the solvent is 164 AMU, this would be the equivalent of 12 mmols of solvent. The cardiovascular system contains 3 mmol of albumin molecules, where each albumin molecule only has a few binding sites. Assuming only 1 binding site per albumin molecule is available, the solvent dose exceeds the binding capacity of the albumin.

The microdroplets would circulate through the cardiovascular system. Gradually, molecules from the microdroplets would break away and dissolve into the blood plasma. Upon breaking free from the microdroplet, the individual lipid molecules would then bind to blood albumin, if albumin with free binding sites are available. Depending on the solubility of the microdroplets, the rate limiting step would either be the solubility of the microdroplet compound or the speed at which blood albumin can bind to the biocompatible solvent molecules and transport them back to the liver or adiposities. The rate at which lipid molecules break free from the microdroplet and dissolve into the blood plasma would largely depend on the solubility of the biocompatible solvent means in blood plasma. Ideally we want the microdroplet to circulate in the cardiovascular system as a discrete droplet until it attaches to plaque and as such very low solubility in blood plasma is desired.

Atherosclerotic disease progresses very slowly. The arteries gradually accumulate plaque and narrow over many decades. If a small quantity of plaque can be removed with each injection, it would be possible to stop the progression of atherosclerosis and actually reverse the disease. A typical adult may accumulate on average 1-2 grams of atherosclerotic plaque per year. If a senior citizen were to receive a weekly injection of biocompatible microdroplet solvent emulsion, even if only 38 mg of cholesterol is dissolved per dose, this would be sufficient to halt and reverse the disease.

It is important to reiterate that under normal circumstances the concentration of unbound free fatty acids and other water insoluble lipids which are circulating in human blood is very low. A study conducted by Goodman[8], concluded that the concentration of unbound fatty acids in bodily fluids is on the order of 10 nanomolar. As such, in 1 litre of blood we would expect approximately $10^{-8}$ moles of fatty acid molecules, and assuming an average molecular weight of 200 AMU this would correspond to about 2 micrograms per litre. It is interesting to note that this number is actually smaller than the solubility of cholesterol in pure water, which is approximately 95 micrograms per litre at 30° C. The main reason for the difference is that in the case of blood, the fatty acids are not allowed to dissolve until the saturation concentration is achieved, but rather bind with blood proteins and are removed from circulation as they become available. The concentration of free fatty acids in human blood is actually much lower than in pure water, due to the effectiveness with which albumin blood protein binds with the free fatty acid molecules.

The output from FIGS. 6 and 7 is a biocompatible solvent/saline mixture, which may be emulsified prior to being packaged. If however the microdroplets have coalesced, it may be necessary to repeat the emulsification step at the point of use, prior to administration. A portable emulsifier can be provided to medical clinics, which can rapidly and cost effectively emulsify the biocompatible microdroplet solvent emulsion means prior to its use. A sealed, sterilized tube 301 is prepared which contains isotonic saline 311 as well as a water insoluble biocompatible solvent means 310. This sterilized tube would be produced in a factory or lab and shipped to hospitals or medical clinics as a finished product. Preferably, but not necessarily, the lid 313 of tube 301 will have a diaphragm 312 which can be punctured to extract the biocompatible solvent using a needle once the ultrasonic emulsification is complete.

Since we desire that the microdroplets have a low surface energy density with cholesterol, they must forcibly have a high surface energy density with saline, and the emulsion will likely exhibit poor thermodynamic stability. As such, a portable ultrasonic emulsifier 300 is used to emulsify the biocompatible microdroplet solvent shortly prior to use. Ultrasonic emulsification is used to ensure the microdroplets are sufficiently small to prevent embolisms in the small capillaries of the lung or other vital organs. Experiments have shown that microdroplets with a diameter of 4 microns or less do not pose a risk of embolism, and that high intensity ultrasonic emulsification is capable of producing microdroplets with a diameter significantly less than 1 micron. The size and distribution of the microdroplet diameters depends on the time and intensity the ultrasonic energy was applied. Portable ultrasonic emulsifier 300 comprises of a high power radio frequency power source 305. The frequency of excitation can vary from one design to another, but will typically be between 10 kHz and 100 kHz for the purposes of generating a micro or nano emulsion. The radio frequency energy is used to excite ultrasonic transducers 302 and cause them to vibrate and generate an ultrasonic wave. The ultrasonic energy from ultrasonic transducers 302 is guided to the sample using an ultrasonic horn 303. The ultrasonic horn 303 will usually be fabricated from metal, and be shaped like a wedge to guide the ultrasonic energy towards the sample being emulsified. The intensity of the ultrasonic energy increases as it travels from the transducer, to the tip of the wedge. The sealed and sterilized test tube 301 is clamped between the two ultrasonic wedges. The narrow end of the wedges 303 has a semi-cylindrical indentation 304, with a compliant rubber lining to allow for good acoustic contact between the ultrasonic horn 303 and the test tube 301 thereby ensuring the ultrasonic energy propagates from the horn into the sample.

The time and intensity of the ultrasonic waves needed to ensure the microdroplets have a diameter of 4 microns or less will depend on the compounds used to fabricate the biocompatible microdroplets as well as the strength and intensity of the ultrasonic emulsifier but will usually be less than 20 minutes. A timer and control module can be provided as part of the portable ultrasonic emulsifier to ensure the sample has been properly emulsified. The diagram provided here shows two ultrasonic transducers 302 and two ultrasonic wedges 303 to excite the sample with ultrasonic energy form both directions. In practise, alternative embodiment could use a single ultrasonic transducer and a single ultrasonic wedge and simply clamp the sample against the single wedge. This type of design, although less expensive, would require more time to emulsify the biocompatible sample, and given the criticality of ensuring the microdroplets are sufficiently small to prevent embolisms, two transducers and two wedges seem preferable.

Once emulsified, the medical personnel can extract the emulsified biocompatible microdroplet solvent by puncturing diagram 312 with a need/syringe and drawing the emulsion into the said syringe. Alternatively, the cap can be unscrewed and the biocompatible microdroplet solvent emulsion means can be drawn directly into a syringe and injected. The microdroplet emulsion should then be injected into the patient before the microdroplets have had a chance to coalesce. Preferably, an inline filter to remove microdroplets of biocompatible solvent in excess of about 4 microns should be used Once in the cardiovascular system of the patient, the microdroplets will be mixed randomly by the cardiovascular system, in a blood volume of approximately 4 litres, and the probability that multiple microdroplets collide and make contact is relatively small. Within a few minutes a majority of the microdroplets should have come into contact with arterial plaque along the walls of the arterial system, and will have attached to the plaque, and will dissolve cholesterol.

The preferred emulsification means is ultrasonic emulsifier 300, however other methods of emulsifying the biocompatible solvent with saline could be used. The emulsification means could comprise of a portable ultrasonic emulsifier or a mechanical homogenizer. Other emulsifications means which make use of nano structures, such as very fine meshes to break up the lipid phase and form microdroplets could also be used. In essence, the emulsification means could be any process which can break up the water insoluble biocompatible droplet and the aqueous phase saline into a micro emulsion.

When the biocompatible microdroplet solvent emulsion means is injected into an artery to provide a focus treatment to a specific artery, or for individuals who are hospitalized it may be preferable to administer the solution slowly, at a very specific rate. This could be accomplished using the apparatus shown in FIG. 8. The biocompatible microdroplet solvent emulsion could be stored in reservoir 601. Optionally, stirring could be provided or ultrasonic energy could be injected into the reservoir to prevent the solvent/saline mixture from separating. An infusion pump 605 can be used to pump the biocompatible microdroplet solvent means at a very precise rate. Optionally the infusion pump 605 can be controlled by a computer or control module to follow a very precise dosing protocol. After the infusion pump, a final emulsification step is provided by Inline Ultrasonic emulsifier 608. The inline emulsification can be achieved by passing the IV line through a grove at the tip of the ultrasonic horn, to ensure high energy ultrasonic energy penetrates the IV line and breaks up any larger droplets. Immediately after the inline ultrasonic emulsifier, a filter 606 is provided to trap any microdroplets in excess of the desired maximum droplet diameter, which would typically be about 4 microns. The final element is the connector 607 for connecting the device to an IV line, as is generally done in a hospital environment. Use of the apparatus in FIG. 8 would allow a very precise dosing protocol to be administered for patients who have recently had a heart attack or stroke or are at imminent risk of having a heart attack or stroke.

If a specific blockage is being treated, it may be beneficial to remove microdroplets of the biocompatible solvent from a patient's cardiovascular circulation, to allow a greater quantity of biocompatible microdroplet solvent emulsion means to be injected through arterial catheter 603. Given that the microdroplets are smaller than blood cells, it is not possible to separate them using mechanical means such as a filter. Two methods which could be employed is an inline centrifugal separator, or to leverage surface energy of the microdroplets, and their affinity to hydrophobic surfaces. For biocompatible solvents which have a density either lower or higher than blood and its components, an inline centrifuge could allow the solvent microdroplets to be separated from the blood. Preferably however, a long line of specially formulated IV line, with a large internal surface that will have a very low surface energy density with the microdroplets, could be used to cause the microdroplets to accumulate on the inner surface of the line. Microdroplets of the biocompatible solvent which come into contract with the surface of this specially formulated IV line would stick or bind to the interior surface of the line. Prior to allowing the blood to flow back to the patient, a droplet filter would be used to ensure a large droplet of biocompatible solvent which would have coalesced within the filter does not reinter the patient's cardiovascular system. A small infusion pump could be used to push a small but steady flow of blood through this specially formulated IV line.

An alternative to generating a microemulsion in a saline solution would be to inject the biocompatible solvent means using a specially designed catheter with micromachined perforations/holes at its tip. Referring now to FIG. 9, one can see a cylindrical micromachined catheter tip 800 which could be fastened to the tip of a catheter. The catheter tip 800 is specially designed to have thin wall thickness, and has micromachined holes/pores 801 on the lateral surface of the catheter tip, and holes/pores 802 on the front tip of the catheter. The micromachined hole diameter must preferably be on the order of 1 micron or less, but should definitely be less than 10 microns. The hole diameter must be small to ensure that the microdroplets which are created have a diameter of 4 microns or less. The exact hole diameter which results in microdroplet of 4 microns or less will ultimately depend on the pressure with which the biocompatible solvent is being pushed through the micromachined holes, as well as the viscosity of the biocompatible solvent means. Using modern micromachining techniques it is possible to etch or create perforations of such a small size. For example, using photolithographic techniques as are commonly used for the manufacture of semiconductors, printed circuit boards or MEMs, it is possible to form patterns and shapes which are smaller than 300 nm on the surface of an object. A light sensitive photoresist in used to coat the cylindrical catheter tip. A photomask is used to cover the photoresist, and the whole is exposed to light, and then developed. The end result is an array of holes in the photoresist. Once the photoresist has been patterned, etching holes through a catheter can be achieved using wet etch, anisotropic plasma etching, laser drilling or other techniques. The catheter tip 800 could be made of stainless steel, a hard ceramic or even a polymer or any other material which can be used intravenously and lends itself well to micromachining. The catheter tip would be bonded to a catheter tube 811, to form the catheter shown in FIG. 10. Given the extremely small size of the individual holes 801 and 802, a large number of holes are needed to allow the biocompatible solvent to flow through the micromachined holes with a reasonable flow rate, without needing excessively high pressures.

Once catheter 810 is inserted into an artery or vein, as the biocompatible solvent means is pushed through the micromachined holes, the flowing blood and high surface tension between the blood plasma and biocompatible solvent means causes microdroplets to be formed. The microdroplets are then pulled downstream by the flowing blood and distributed within the cardiovascular system.

The advantage of using this specially formulated catheter tip, is that the biocompatible solvent means can be directly injected into a patient's blood stream, without first needing to be emulsified using high energy ultrasound. Furthermore, there is no risk that a large droplet of solvent which has not been sufficiently broken down by ultrasonic energy enter the cardiovascular system. The catheter tip could have a diameter which is typical of arterial or veinous catheters. Furthermore, as opposed to a blunt tip, the catheter could be designed to have a pointy tip to puncture a vein directly. For an embodiment of catheter tip 300 with a pointy tip.

This biocompatible microdroplet solvent emulsion means would find many applications. It could be administered to a patient as a periodic treatment to slow the progression, prevent or reverse atherosclerosis. The ability to prevent or reverse atherosclerosis would significantly reduce the incidence of heart disease and stroke. Furthermore, there is increasing evidence that atherosclerosis is linked with Alzheimer's, dementia and other forms of cognitive decline in the elderly, and the biocompatible microdroplet solvent emulsion means would find applications here as well. For patient's which have had a heart attack or stroke, or are considered to be in imminent risk of having a heart attack or stroke, the patient could be admitted to the hospital, and a prolonged treatment lasting several days could be initiated to rapidly reduce the accumulated plaque from a patient's arteries. For a patient which is known to have an artery with restricted blood flow due to arterial plaque, the biocompatible microdroplet solvent emulsion means could be used in conjunction with an arterial catheter to provide a more focused treatment to a specific artery, and administered using the apparatus similar to that shown in FIG. 8. Two methods of generating the microdroplets have been proposed. The first is to emulsify the biocompompatible solvent means with saline using high intensity ultrasonic energy. The result of this process is a biocompatible microdroplet emulsion means which comprises of an aqeuous carrier in which are suspended the microdroplet of the biocompatible solvent. A second method which has been proposed is to generate the microdroplets directly within the cardiovascular system using a novel catheter with a special micromachined tip with an array of pores/holes which are on the order of 1 micron in diameter. The cross section of the micromachined holes must be small enough to ensure that the microdroplets have a diameter of about 4 microns or less.

Alternative Embodiments

The preferred embodiment of the invention has identified a novel biocompatible microdroplet solvent emulsion means which can be administered intravenously to bring about a reversal and reduction of atherosclerosis. We have provided a list of various compounds which have both low toxicity to humans, a low solubility in the water based blood to allow the microdroplets to travel as discrete entities within the cardiovascular system, as well as a good solubility match with cholesterol, cholesterol esters and other components of plaque to ensure dissolution of plaque. The compounds are listed in tables 1, 2, 3 and 4 and are described within the body of the patent in greater detail. Most of our focus has been on fatty acids, terpenes, terpanoids, monoterpene keytones, monoterpene alcohols, sesquiterpene alcohols as well as acetates, benzoates and ethers. The compounds identified occur naturally in foods, herbs and spices and are safe for human consumption in modest quantities. However, other types of organic molecules could potentially be used. It is conceivable that molecules from the Organometallic family, Nitro family, Nitrile family, Aminine family, Amide family, Carboxylic acid chloride family, Ester family, Ketone family, Aldehyde family, Carbonyl family, Ether family, Halide family, Arene family, Alkyne family or Alkene family. Also, longer chain alcohols which are not water soluble and found to have acceptable levels of toxicity could potentially be considered as one of the components of the biocompatible solvent. It should be understood that microdroplets could be fabricated from other compounds, or mixtures of different compounds, which are not explicitly stated within this patent, without departing from the spirit of the invention.

Furthermore, we have shown from energy principals that the microdroplets can be made selective to free cholesterol and other components of arterial plaque by designing the microdroplets to have a low surface energy with cholesterol, relative to a higher surface energy when coming into contact with blood, blood cells, endothelial cells or other structures within the cardiovascular system. Since the microdroplets are designed to have a low surface energy when coming into contact with cholesterol, and to have a good solubility match with cholesterol, the microdroplets will have a tendency to bind to cholesterol in-vivo, as opposed to other surfaces, thereby providing a very focused and selective means of dissolving arterial plaque. The implication of designing the microdroplets to have a low interfacial surface energy density with cholesterol, and a high interfacial surface energy density with hydrophilic surfaces is that the microdroplets will have a tendency to coalesce, and the emulsion will not be stable over an extended time period, or at least less stable than if a surfactant had been used to reduce the surface energy density at the microdroplet/aqueous interface. Unlike pharmaceutical emulsions which are developed to aid in the delivery of water insoluble drugs and a surfactant is used to reduce the surface energy density at the microdroplet/aqueous surface interface, to prevent microdroplets from coalescing and to achieve long term thermodynamic stability, the use of a surfactant is not advisable for the purposes of this invention. To achieve a high level of selectivity, the interfacial surface energy density of the microdroplet must be high when contacting blood, the membrane of blood cells or endothelial cells, but relatively low when contacting cholesterol or cholesterol esters in plaque. However, it is conceivable that a small quantity of surfactant could be used without significantly altering the surface energy of the microdroplets, and that they would nevertheless selectively bind to cholesterol when injected intravenously. Furthermore, the use of a component which is partially miscible in both water and the biocompatible solvent, such as a water soluble alcohol, could be used to adjust the surface energy density of the microdroplets. Furthermore, use of an alcohol, which is soluble in both saline and the microdroplets might help improve the thermal stability of the emulsion while in storage, but diffuse out of the droplet after it has been administered intravenously. The inventive step is not so much whether or not a surfactant is present, but rather that the microdroplets have a low surface energy when coming into contact with arterial plaque, and a high surface energy density when coming into contact with blood cells or endothelial cells, as well as at the blood/microdroplet interface. Use of a surfactant as is generally done when preparing emulsions will reduce the surface energy at the microdroplet/aqueous interface and cause the microdroplet to no longer selectively attach to cholesterol, cholesterol esters or other components of arterial plaque. Furthermore, use of an ultrasonic emulsifier has been proposed to provide high energy microdroplet emulsification at the point of care, prior to injecting the microdroplet biocompatible solvent emulsion within a patient. However, other means could be used to create the emulsion, such as homogenization, or using microfluidic methods such as passing the solvent and saline through a micromachined mesh, without departing from the spirit of the invention. For this purpose, a novel catheter with a micromachined tip has been proposed. The micromachined tip has an array of holes with a diameter of a few microns, and as the biocompatible solvent is pushed through these holes into a vein or artery, microdroplets are naturally formed.

This same catheter with a micromachined tip, could be used to generate a stream of microdroplets in a saline line, just prior to having the saline flow into the patient. This special tip would allow the biocompatible solvent means to be directly injected into a saline line and cause the microdroplets to be generated as the biocompatible solvent flows through the micromachined pores into the saline.

INDUSTRIAL APPLICABILITY

A pharmaceutically acceptable biocompatible microdroplet solvent emulsion which can be safely administered intravenously to bring about a reduction in the accumulation of atherosclerotic plaque within a patient is provided. The microdroplets from which the emulsion is comprised are designed to have solubility parameters which are well match to cholesterol, cholesterol esters and other components of arterial plaque. Furthermore, by designing the microdroplets to have a low interfacial surface energy density when coming into contact with free cholesterol within the plaque, relative to being suspended in blood plasma or in contact with other surfaces such as the phospholipid bilayer of blood cells or endothelial cells, helps ensure the microdroplets selectively attach and dissolve plaque. Since the microdroplet emulsion will not be thermodynamically stable for extended durations, an ultrasonic emulsifier is also provided which can be used at the point of care prior to intravenous administration. In addition, a novel catheter with a micromachined tip is also proposed specifically to allow the microdroplets to be generated intravenously, as an alternative to emulsification with saline. Given that heart disease and stroke remain the leading cause of death in the developed world, there is a great need for new technologies and ideas within the medical community and the inventions described herein should find widespread acceptance and use. In addition to treating blockages in larger arteries of the heart and brain, the microdroplets will travel through all blood vessels and the invention has applicability to treating atherosclerosis in small vessels of the brain and heart. Atherosclerosis is the small arteries of the brain are often referred to as cerebral small vessel disease, small vessel ischemic disease, white matter disease, periventricular white matter changes, perivascular chronic ischemic white matter disease of aging, white matter hyperintensities, age-related white matter changes and leukoaraiosis. When the small arteries of the heart are impaired due to atherosclerosis, this condition is known as coronary microvascular disease (MVD). Coronary MVD as well as cerebral small vessel disease cannot be treated using angioplasty given the small size and large number of arteries affected. Finally, a significant body of new research is showing a strong correlation between Alzheimer's and atherosclerosis in the vessels of the brain, and as such the invention disclosed herein could find applications for treating these patients as well.

REFERENCES

1. Wikipedia reference on Atheroma, http://en.wikipedia.org/wiki/Arterial_plaque
2. Shipra Baluj a et al., "Solubility of Cholesterol in some alcohols from 293.15 to 318.15K", Archives of Applied Science Research, 2009, 1 (2) pp. 263-270.
3. "Hansen's Solubility Parameters a Users Handbook" Second Edition, by Charles M. Hansen, CRC Press
4. Cutnell, John & Johnson, Kenneth. *Physics, Fourth Edition*. Wiley, 1998: 308.
5. John McMurry, "Fundamentals of Organic Chemistry", Brooks/Cole Publishing Company, 1986.
6. Ger J. van deer Vusse, "Albumin as Fatty Acid Transporter", Drug Metab. Pharmacokinet. 24 (4):300-307, 2009.
7. Goodman, D. S.: "The Interaction of Human Serum Albumin with Long-chain Fatty Acid Anions", Journal of American Chemical Society, 80: 3892-3898, 1958.

The invention claimed is:

1. A method of dissolving cholesterol in a subject diagnosed with atherosclerosis comprised of administering microdroplets intravenously where the said microdroplets are comprised of one or more hydrophobic water insoluble compounds, have solubility properties such that their Relative Energy Difference (RED) with cholesterol be 1.0 or less, and have an interfacial surface energy density with cholesterol which is lower than their interfacial surface energy density with blood plasma.

2. A method of dissolving cholesterol according to claim 1 where the said cholesterol is a component of arterial plaque.

3. A method of dissolving cholesterol according to claim 2 where the said microdroplets have a relative energy difference (RED), as defined by Hansen Solubility Theory, of less than 0.8 with cholesterol.

4. A method of dissolving cholesterol according to claim 2 where the said microdroplets have a relative energy difference (RED) of less than 0.7 with cholesterol, as defined by Hansen Solubility Theory.

5. A method of dissolving cholesterol according to claim 2 where the said microdroplets have a relative energy difference (RED) of less than 0.6 with cholesterol, as defined by Hansen Solubility Theory.

6. A method of dissolving cholesterol according to claim 2 where the said microdroplets have a relative energy difference (RED) of less than 0.4 with cholesterol as defined by Hansen Solubility Theory.

7. A method of dissolving cholesterol according to claim 4 where the said microdroplets comprise of one or more monounsaturated fatty acid or polyunsaturated fatty acids such as Alpha-linolenic acid (ALA Omega 3), Linoleic acid (an Omega 6), oleic acid (an Omega 9), Eicosapentaenoic acid (EPA Omega3), Docosahexaenoic Acid (DHA Omega 3).

8. A method of dissolving cholesterol according to claim 2 where the said microdroplets are administered as part of an emulsion with saline.

9. A method of dissolving cholesterol according to claim 2 where the said microdroplets are generated directly in a blood vessel by pushing the said one or more hydrophobic water insoluble compounds through a micromachined catheter tip.

10. A method of dissolving cholesterol according to claim 1 where the said cholesterol is associated with a risk of one or more of a heart attack, a stroke, or is related to one of atherosclerosis, Alzheimer's disease, dementia, or Small Artery Disease in the heart or brain.

11. A method of dissolving cholesterol according to claim 10 where the said microdroplets comprise of one or more of 1,8 cineole, carvacrol, menthol, acetophenone, myrcene, ocimene, geraniol, nerol, citronellol, Artemisia ketone, citral, citronellal, linalyl acetate, dipentene, terpinolene, limonene, phelladrene, sylvestrene, perillaldehyde, pulegone, piperitone, menthone, 1,4 cineole, farnesol, nerolidol, bisabolene, zingiberene, diethyl carbonate.

12. A method of dissolving cholesterol according to 10 where the said microdroplets comprise of one or more of eugenol, carvone, 1,8 cineole.

13. A method of dissolving cholesterol according to claim 10 where the said microdroplets comprise of one or more of benzyl benzoate or diphenyl ether.

14. A method of dissolving cholesterol according to claim 10 further characterized by use of:

a. A pharmacologically acceptable emulsion of hydrophobic microdroplets in a water based carrier.

15. A method of dissolving cholesterol according to claim 14 where the said water based carrier comprises of a saline solution.

16. A method of dissolving cholesterol according to claim 15 where the microdroplets are formulated to have a relative energy difference (RED) with cholesterol, cholesterol esters or other component of arterial plaque of 0.8 or less, as defined by Hansen's Solubility Theory.

17. A method of dissolving cholesterol according to claim 15 where the said microdroplets have an interfacial surface energy density with one of cholesterol, cholesterol esters or another component of plaque which is less than the surface energy density between the microdroplets and one of blood plasma and the outer surface of blood cells or endothelial cells.

18. A method of dissolving cholesterol according to claim 1 further characterized by use of a specially designed injection means for the intravenous administration of a hydrophobic compound where:

a. The injection means has one or more holes with a sufficiently small cross section to ensure that microdroplets are formed as the said hydrophobic compound is pushed through the said injection means into the cardiovascular system.

19. A method of dissolving cholesterol according to claim 18 where the said holes are located on the frontal or lateral surfaces of the tip of the said injection means and have a diameter of 10 microns or less.

20. A method of dissolving cholesterol according to claim 18 where the said holes in the said specially designed injection means are created using one or more of photolithographic techniques or laser drilling, or other micromachining technique.

* * * * *